Figure 1:
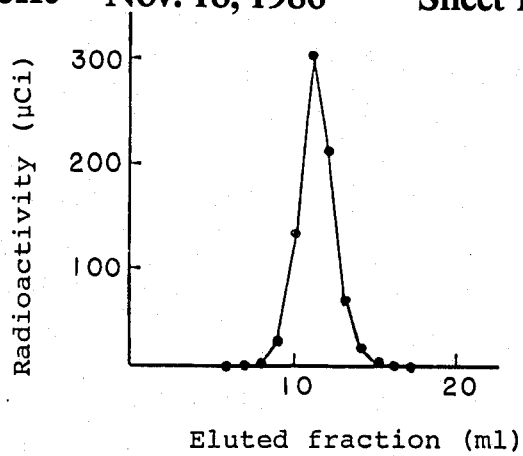

United States Patent [19]

Kono et al.

[11] Patent Number: 4,623,485
[45] Date of Patent: Nov. 18, 1986

[54] 4- OR 6-SUBSTITUTED ALDOSTERONES

[75] Inventors: Masao Kono, Ibaraki; Taichitro Komeno, Osaka; Shoichi Ishihara, Toyonaka; Akira Yamauchi, Osaka; Tadashi Okabayashi, Nishinomiya, all of Japan

[73] Assignee: Shionogi & Co., Ltd., Osaka, Japan

[21] Appl. No.: 493,280

[22] Filed: May 10, 1983

[30] Foreign Application Priority Data

May 10, 1982 [JP] Japan .................................. 57-78847

[51] Int. Cl.[4] .......................... C07J 41/00; C07J 43/00
[52] U.S. Cl. ..................................... 540/92; 435/174; 435/188
[58] Field of Search ................ 260/239.55 R; 435/174

[56] References Cited

U.S. PATENT DOCUMENTS 2,973,357  2/1961  Johnson et al. ............ 260/239.55 R

OTHER PUBLICATIONS

Greene, Protective Groups in Organic Synthesis, 1981, pp. 125–219.

Primary Examiner—Richard L. Raymond
Attorney, Agent, or Firm—Wenderoth, Lind & Ponack

[57] ABSTRACT

A substituted aldosterone of the formula:

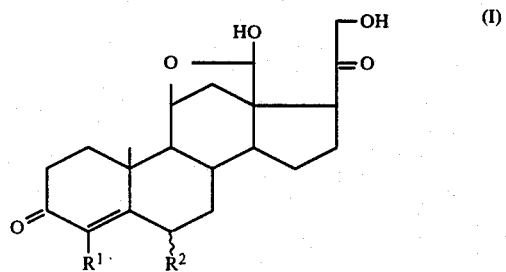

wherein either one of $R^1$ and $R^2$ is hydrogen and the other is $-S(CH_2)_mCOR^3$ or $-OCO(CH_2)_nCOR^3$, provided that when $R^1$ is hydrogen, $R^2$ is $-S(CH_2)_mCOR^3$ or $-OCO(CH_2)_nCOR^3$ and when $R^2$ is hydrogen, $R^1$ is $-S(CH_2)_mCOR^3$; m being an integer from 1 to 3, n being an integer from 1 to 5 and $R^3$ being hydroxyl, lower alkoxy or a residue of tyramine, tyrosine lower alkyl ester, histamine, histidine, 7-aminoheptanoyltyrosine lower alkyl ester or β-D-galactosidase as optionally iodinated, or its (18–20)-acetal 20,21-ketonide, which is useful as the reagent in determination of aldosterones by radioimmunoassay or enzyme immunoassay.

2 Claims, 7 Drawing Figures (Anti-serum is anti-compound (I: $R^1$ = H; $R^2$ = α-OCOCH$_2$CH$_2$COOH)-BSA)

4- OR 6-SUBSTITUTED ALDOSTERONES

The present invention relates to substituted aldosterones, which are useful in determination of aldesterone (hereinafter referred to as "ALD") by radioimmunoassay (hereinafter referred to as "RIA") or enzyme immunoassay (hereinafter referred to as "EIA").

Among various steroid hormones, determination of ALD has been considered most difficult, and conventional immunoassay is not satisfactory for determination of ALD. In general, the adequacy of immunoassay depends much on aptitude of antihapten antiserum employed therein, characteristics of which vary with the structure of immunogen. For immunogen, compounds having functional groups in a free state as many as possible are considered to be desirable.

As the hapten of ALD, there are known its 21-hemisuccinate, 3-(O-carboxymethyl)oxime, 18,21-bishemisuccinate, etc.; however, all of them are at least partly blocked in their functional groups and hence are not satisfactory.

Considering the above situation, the present inventors have attempted to provide haptens of ALD which have all the functional groups of ALD in a free state and now succeeded in providing such haptens.

Accordingly, a main object of the present invention is to provide substituted aldosterones available as haptens of aldosterones. Another object of this invention is to provide a process for preparation of said substituted aldosterones. A still other object of the invention is to provide anti-hapten antisera by the use of said haptens. A further object of the invention is to provide labelled antigens by the use of said haptens. A still further object of the invention is to provide a method of RIA or EIA of ALD using said anti-hapten antisera or labelled antigens. A still further object of the invention is to provide a kit for RIA or EIA examination using said anti-hapten antisera or labelled antigens. These and other objects will be apparent to those skilled in the art from the foregoing and subsequent descriptions.

The substituted aldosterones of the invention are represented by the formula:

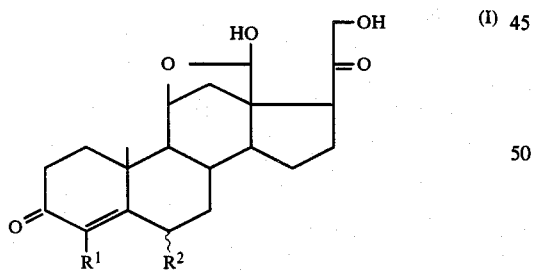

wherein either one of $R^1$ and $R^2$ is hydrogen and the other is $-S(CH_2)_mCOR^3$ or $-OCO(CH_2)_nCOR^3$, provided that when $R^1$ is hydrogen, $R^2$ is $-S(CH_2)_mCOR^3$ or $-OCO(CH_2)_nCOR^3$ and when $R^2$ is hydrogen, $R^1$ is $-S(CH_2)_mCOR^3$; m being an integer from 1 to 3, n being an integer from 1 to 5 and $R^3$ being hydroxyl, lower alkoxy or a residue of tyramine, tyrosine lower alkyl ester, histamine, histidine, 7-aminoheptanoyltyrosine lower alkyl ester or β-D-galactosidase as optionally iodinated (particularly radioiodinated). Specific examples of $-S(CH_2)_mCOR^3$ are carboxymethylthio, carboxylethylthio, carboxypropylthio, etc. and specific examples of $-OCO(CH_2)_nCOR^3$ are hemimalonyloxy, hemisuccinyloxy, hemiglutaryloxy, hemiadipoyloxy, hemipimeloyloxy, etc.

Of these substituted aldosterones (I), the compounds wherein $R^3$ is a hydroxyl group may be combined with proteins such as bovine serum albumin. Immunization of rabbits with the resulting products as antigens gives anti ALD antiserum. They may be also combined with enzymes for labelling such as horseradish peroxidase, alkalinephosphatase, β-D-galactosidase and glucosidase to give labelled products for EIA. Examples of suitable substituted aldosterones (I) are (11β,18-epoxy-18α,21-dihydroxy-3,20-dioxo-4-pregnen-4-ylthio)acetic acid, (11β,18-epoxy-18α,21-dihydroxy-3,20-dioxo-4-pregnen-6β-ylthio)acetic acid, 11β,18-epoxy-18α,21-dihydroxy-3,20-dioxo-4-pregnen-6α or 6β-yl hemisuccinate, etc.

The substituted aldosterones (I) wherein $R^3$ is other than hydroxyl may be labelled with radioiodine such as $^{125}I$ or $^{131}I$ according to a conventional Chloramine-T or enzymatic method to give a labelled product for RIA. Examples of suitable substituted aldosterones (I) are N-(p-hydroxyphenethyl)-2-(11β,18-epoxy-18α,21-dihydroxy-3,20-dioxo-4-pregnen-4-ylthio)acetamide, 11β,18-epoxy-18α,21-dihydroxy-3,20-dioxo-4-pregnen-6α or 6β-yl 4-(p-hydroxyphenethylamino)-4-oxobutyrate, etc.

The substituted aldosterones (I) can be produced, for instance, by subjecting a compound of the formula:

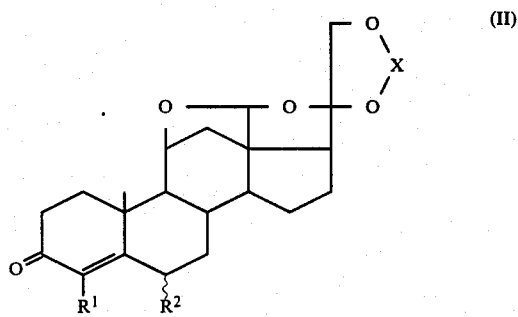

wherein $R^1$ and $R^2$ are each as defined above and X is a glycol protective group to elimination of the protective group.

The conversion of the compound (II) into the compound (I) as well as the production of the compound (II) as the starting material are summarized shown in the following scheme:

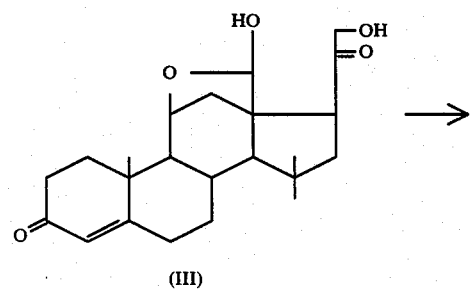

-continued

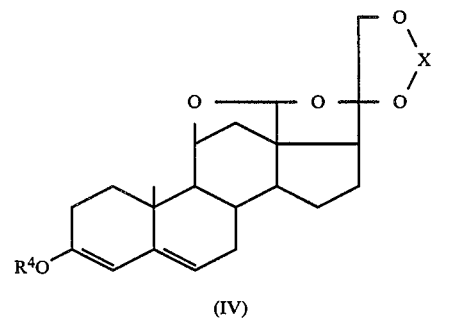

(IV)

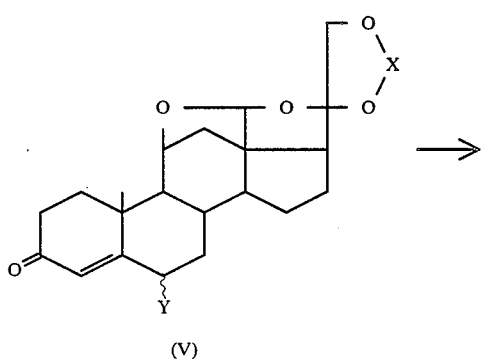

(V)

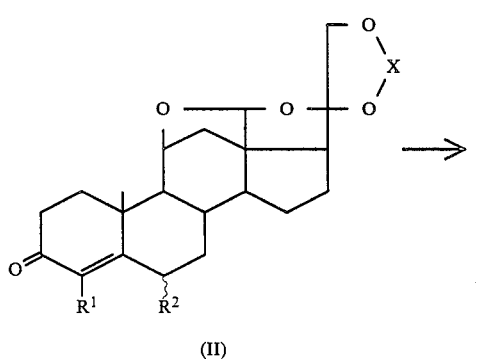

(II)

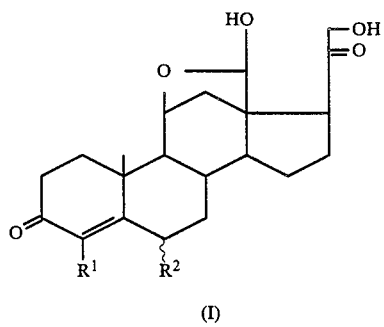

(I)

wherein R¹, R² and X are each as defined above, R⁴ is a lower alkyl group and Y is a hydroxyl group or a bromine atom.

In the above scheme, the starting hemiacetal-type ALD, i.e. 11β,18-epoxy-18α,21-dihydroxy-4-pregnene-3,20-dione (III), is enol-etherified on the carbonyl group at the 3-position and simultaneously protected on the hydroxyl groups at the 20- and 21-positions as an acetonide to give the compound (IV). The compound (IV) is converted into the compound (V) wherein Y is a bromine atom by bromination, or into the compound (V) wherein Y is a hydroxyl group by treating with a peracid such as m-chloroperbenzoic acid or monoperphthalic acid.

The compound (V) wherein Y is a bromine atom is reacted with sodium methyl thioglycolate (NaSCH₂COOCH₃) to give the corresponding acetate derivative (II') wherein either R¹ or R² is hydrogen and the other is SCH₂COOCH₃. The acetate derivative (II') thus obtained is hydrolyzed under basic conditions, for instance, by treatment with potassium carbonate in aqueous methanol under nitrogen stream at room temperature 1-6 hours to give the corresponding acetic acid derivative (II) wherein either R¹ or R² is hydrogen and the other is SCH₂COOH.

Also, the compound (V) wherein Y is a hydroxyl group is reacted, for instance, with succinic anhydride under basic conditions, e.g. by treatment with succinic anhydride in the presence of 4-dimethylaminopyridine as a catalyst in pyridine while warming (30°-70° C.) for 24 to 63 hours to give the corresponding hemisuccinyl derivative (II) wherein R¹ is hydrogen and R² is OCOCH₂CH₂COOH.

The acetic acid or hemisuccinyl derivative (II) as prepared above is reacted with tyramine in the presence of 1-hydroxybenzotriazole and dicyclohexylcarbodiimide in tetrahydrofuran while ice-cooling for 7 to 21 hours to give the tyramine-conjugated compound (II) wherein either R¹ or R² is hydrogen and the other is

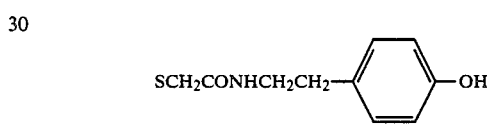

or R¹ is hydrogen and R² is

In this reaction, tryamine may be replaced by any other compound having an amino group so that the corresponding carbonamide compound is obtainable as the compound (II).

The thus obtained compound (II) is subjected to elimination of the protective group, preferably at room temperature in an inert gas under acidic conditions, to give the corresponding unprotected compound (I) such as (11β,18-epoxy-18α,21-dihydroxy-3,20-dioxo-4-pregnen-4 or 6β-ylthio)acetic acid or its amide with tyramine or 11β,18-epoxy-18α,21-dihydroxy-3,20-dioxo-4-pregnen-6β or 6α-yl hemisuccinate or its amide with tyramine.

The elimination of the protective group may be accomplished by per se conventional procedures, for instance, as described in T. W. Greene, "Protective Groups in Organic Synthesis" (1981). Applicable conditions are treatment with mineral acids (e.g. hydrochloric acid, sulfuric acid, perchloric acid), organic acids (e.g. formic acid, acetic acid, propionic acid, p-toluenesulfonic acid), Lewis acids (e.g. BCl₃), acid-type ion-exchange resins, etc. More specifically, there may be adopted treatment with 70% acetic acid for 2-12 hours, treatment with 1N HCl (concentration: 2-20%) in dioxane or tetrahydrofuran, treatment with p-toluenesulfonic acid (concentration: 0.1–1%) in methanol or acetone, or the like.

These compounds (I) may be combined with bovine serum albumin (BSA) to make BSA-conjugates. Using these BSA-conjugates as immunogens, antisera are obtainable. Alternatively, they may be labeled with enzymes to make tracers for EIA or with radioiodine to make tracers for RIA.

For instance, the compound (I) wherein $R^3$ is a hydroxyl group is combined with bovine serum albumin by a per se conventional binding procedure such as the mixed anhydride method to make its BSA conjugate. The BSA conjugate is injected as an immunogen into rabbits several times, and then the blood is collected from the rabbits to obtain an anti-hapten antiserum. The mixed anhydride method as herein stated may be carried out, for instance, by dissolving the compound (I) in dioxane, adding tri-n-butylamine and isobutyl chlorocarbonate thereto and stirring the resultant mixture at a temperature of 8° to 10° C. for 30 minutes. To the reaction mixture containing the active ester, an aqueous dioxane solution containing BSA (adjusted to pH 8.5 with sodium hydroxide) is added, and stirring is continued to give the BSA conjugate of the compound (I). Application of conventional purification procedures to the resulting product affords the material usable as an immunogen. Examples of the purification procedures are dialysis against cold water, adjustment of pH, centrifugation, dissolution into sodium bicarbonate solution, re-dialysis against cold water, etc.

In the above operation, the mixed anhydride method may be replaced by any other binding procedure such as the carbodiimide method (using 1-ethyl-3-(3-dimethylaminopropyl)carbodiimide or 1-cyclohexyl-3-(2-morpholinoethyl)carbodiimide or the isoxazolium method. Still, these binding procedures may be likewise applied when labelling is to be achieved with enzymes. Namely, the only difference is the use of an enzyme in place of BSA [cf. K. Shizume et al.: "Radioimmunoassay, New Edition" published by Asakura Shoten (1977) and E. Ishikawa et al.: "Enzyme immunoassay" published by Igakushoin (1978)].

The labelled antigen for EIA may be prepared, for instance, by labelling the compound (I) wherein $R^3$ is a hydroxyl group with an enzyme by a per se conventional procedure such as the activated ester method. The labelled antigen for RIA may be prepared, for instance, by labelling the compound (I) wherein $R^3$ is other than hydroxyl with radioiodine ($^{125}$I or $^{131}$I) by a per se conventional procedure such as the Chloramine-T method or the enzyme method. In the latter case, atomic iodine obtained by oxidizing iodine ion with Chloramine-T or with the combination of hydrogen peroxide and lactoperoxidase may be introduced into the meta-position of a hydroxyphenyl group [cf. "Radioimmunoassay, New Edition" recited supra].

The immunoassay may be conducted by a method known per se. In case of EIA, determination is achieved, for instance, by comparing the obtained values of the standard solution and a serum to be assayed in measurement of intensity of fluorescence. In RIA, determination is accomplished by comparing the radioactivities of the standard solution and a serum to be assayed, as obtained by the use of a well-type scintillation counter.

Based on the above development, this invention can provide a kit for immunoassay, which comprises (1) ALD as the standard substance, (2) the labelled product of the compound (I) with a radioisotope or an enzyme and (3) an antiserum obtained from the compound (I). Either one of the latter two may be replaced by the one obtained from the known ALD derivative. Optionally, it may contain a buffer solution and an F/B (free/bound)-separating reagent (e.g. PEA) or, in case of the antiserum (3) being used as the first antibody in the two antibody method, a second antibody.

The immunoassay according to the present invention is excellent in sensitivity and cross-reactivity.

The present invention will be illustrated more in detail by the following examples wherein the NMR values indicate those in the spectrum determined with 60 MHz and the Rf values in thin layer chromatography (TLC) show the ones obtained by the use of a precoated silica gel-60 plate (0.25 mm) (manufactured by Merck) unless otherwise indicated.

EXAMPLE 1

Preparation of (11β,18-epoxy-18α,21-dihydroxy-3,20-dioxo-4-pregnen-4-ylthio)acetic acid (I: $R^1=SCH_2COOH$; $R^2=H$):

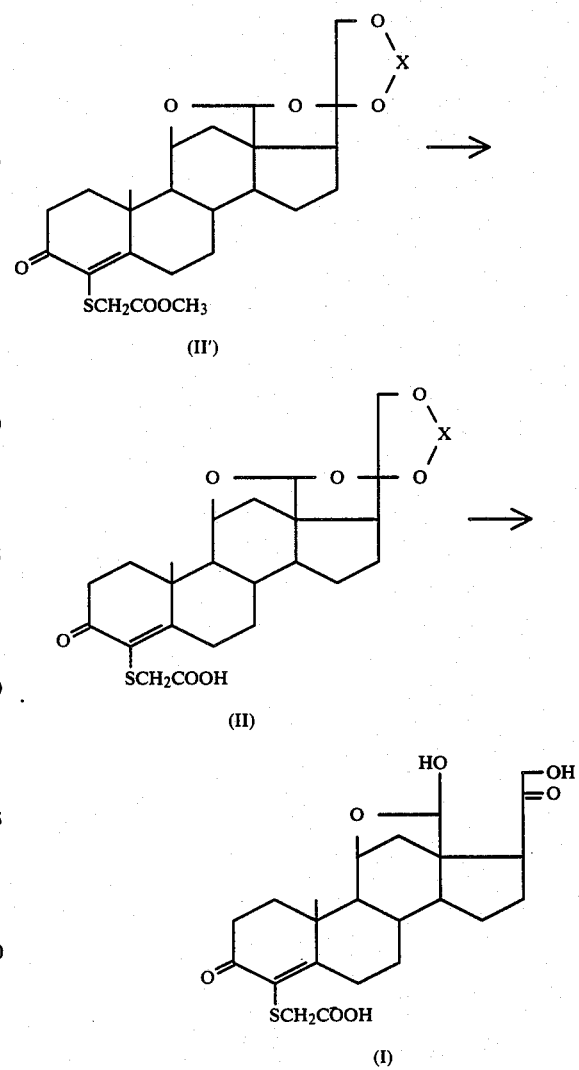

To a mixture of methyl (11β,18;18α,20β-bisepoxy-20α,21-isopropylidenedioxy-3-oxo-4-pregnen-4-ylthio)acetate (II': $R^1=SCH_2COOCH_3$; $R^2=H$; X=20,21(S)- acetonide) (82 mg), methanol (8 ml) and water (4 ml), potassium carbonate (90 mg) was added in nitrogen stream at room temperature, and stirring was continued for 2.5 hours. The reaction mixture was neutralized with acetic acid and extracted with ethyl acetate. The extract was washed with a saturated aqueous sodium chloride solution and dried over anhydrous sodium sulfate, and the solvent was removed under reduced pressure to give (11β,18;18α,20β-bisepoxy-20α,21-isopropylidenedioxy-3-oxo-4-pregnen-4-ylthio)acetic acid (II: R$^1$=SCH$_2$COOH; R$^2$=H; X=20,21(S)-acetonide) as syrupy residue.

NMR (CDCl$_3$, δ): 1.34, 1.50 (9H, 19-H and

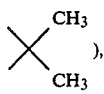

3.38 (2H, s, —SCH$_2$CO—), 3.92, 4.03 (2H, AB$_q$, J$_{AB}$=9 Hz, ν$_{ΔAB}$=6.3 Hz, 21—CH$_2$—), 4.87 (1H, d, J=6 Hz, 11-H), 5.33 (1H, s, 18-H), 7.72 (1H, broad, —COOH).

The above substance was added to a 70% acetic acid solution (3 ml). The mixture was stirred in nitrogen stream at room temperature for 6 hours, combined with ice-water and extracted with ethyl acetate. The extract was washed with a saturated sodium chloride solution and dried over anhydrous sodium sulfate, and the solvent was removed under reduced pressure. The residue was recrystallized from methanol to give (11β,18-epoxy-18α,21-dihydroxy-3,20-dioxo-4-pregnen-4-ylthio)acetic acid (I: R$^1$=SCH$_2$COOH; R$^2$=H) (34 mg) as colorless needles. Yield, 46.7% (based on the starting compound (II′)).

Elementary analysis for C$_{23}$H$_{30}$O$_7$S (450.536): Calcd.: C, 61.31%; H, 6.71%; S, 7.12%.

Found: C, 61.11%; H, 6.95%; S, 6.88%. M.P., 121°–123° C.

[α]$_D^{23}$+136.8±1.7 (c=1.068, chloroform/methanol=1/1).

UV λ$_{max}^{EtOH}$ (nm; ε): 245.5 (10700), 305 (2250).

IR ν$_{max}^{Nujol}$ (cm$^{-1}$): 3470 (sh), 3415, 3238, 2660, 1710, 1672, 1550.

NMR (CD$_3$OD, δ): 1.31, 1.35 (3H, 19-H), 3.44 (2H, s, —SCH$_2$CO—), 3.70 (1H, m, 6α-H), 4.58 (1H, d, J=6 Hz, 11-H), 5.02, 5.43 (1H, 18-H).

Mass spectrum (MS) m/z: 432 (M$^+$−18, <1%), 414 (M$^+$−36, 8%), 342 (M$^+$−108, 4%), 44 (100%), 18 (97%).

In the same manner as above, (11β,18-epoxy-18α,21-dihydroxy-3,20-dioxo-4-pregnen-4-ylthio)acetic acid (I: R$^1$=SCH$_2$COOH; R$^2$=H) was also prepared from methyl (11β,18;18α,20α-bisepoxy-20β,21-isopropylidenedioxy-3-oxo-4-pregnen-4-ylthio)acetate (II′: R$^1$=SCH$_2$COOCH$_3$; R$^2$=H; X=20,21(R)-acetonide) through (11β,18;18α,20α-bisepoxy-20β,21-isopropylidenedioxy-3-oxo-4-pregnen-4-ylthio)acetic acid (II: R$^1$=SCH$_2$COOH; R$^2$=H; X=20,21(R)-acetonide).

The compound (II: R$^1$=SCH$_2$COOH; R$^2$=H; X=20,21(R)-acetonide) showed the following physical constants:

Elementary analysis for C$_{26}$H$_{34}$O$_7$S (490.598): Calcd.: C, 63.65%; H, 6.99%; S, 6.54%. Found: C, 63.72%; H, 6.85%; S, 6.64%.

M.P., 168°–170° C.

[α]$_D^{23}$+104.1±1.4 (c=1.00, chloroform).

NMR (CDCl$_3$, δ): 1.34, 1.40, 1.50 (9H, 19-H and

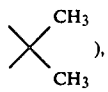

3.37 (2H, s, —SCH$_2$CO—), 3.89, 4.18 (2H, AB$_q$, J$_{AB}$=9 Hz, ν$_{ΔAB}$=17 Hz, 21—CH$_2$—), 4.83 (1H, d, J=6 Hz, 11-H), 5.30 (1H, s, 18-H), 5.90 (1H, broad, —COOH).

Mass spectrum (MS) m/z: 489 (M$^+$−1, 16%), 471 (M$^+$−19, 7%), 400 (M$^+$−90, 20%), 43 (100%).

EXAMPLE 2

Preparation of (11β,18-epoxy-18α,21-dihydroxy-3,20-dioxo-4-pregnen-6β-ylthio)acetic acid (I: R$^1$=H; R$^2$=β-SCH$_2$COOH):

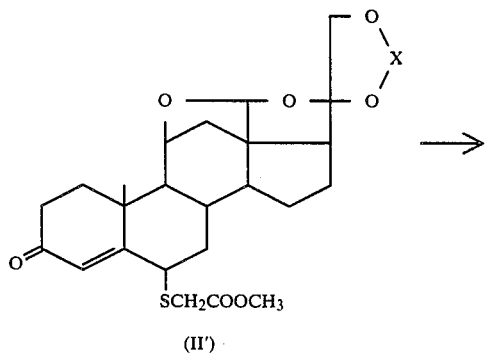

(II′)

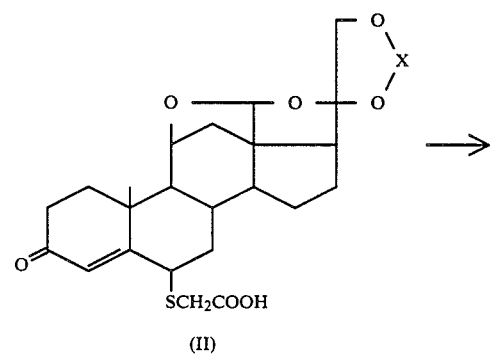

(II)

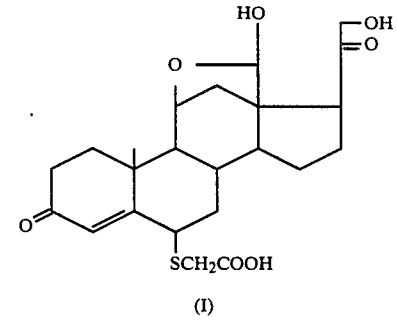

(I)

In the same manner as in Example 1, methyl (11β,18;18α,20β-bisepoxy-20α,21-isopropylidenedioxy-3-oxo-4-pregnen-6-ylthio)acetate (II′: R$^1$=H; R$^2$=β-SCH$_2$COOCH$_3$; X=20,21(S)-acetonide) was treated to give (11β,18-epoxy-18α,21-dihydroxy-3,20-dioxo-4-pregnen-6β-ylthio)acetic acid (I: R$^1$=H; R$^2$=β-SCH$_2$COOH) through (11β,18;18α,20β-bisepoxy-20α,21-isopropylidenedioxy-3-oxo-4-pregnen-6β-ylthio)acetic acid (II: R¹=H; R²=β-SCH₂COOH; X=20,21(S)-acetonide).

Elementary analysis for C₂₃H₃₀O₇S (450.536): Calcd.: C, 58.95%; H, 6.85%; S, 6.84%. Found: C, 58.38%; H, 6.65%; S, 6.31%.

M.P., 164°-166° C.

Mass spectrum (MS) m/z: 414 (M⁺−36, <1%), 44 (45%), 18 (100%).

The compound (II: R¹=H; R²=β-SCH₂COOH; X=20,21(S)-acetonide) showed the following physical constants:

M.P., 210°-213° C.

NMR (CD₃OD, δ): 1.50, 1.54, (9H, 19-H and

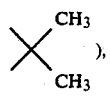

5.41 (1H, s, 18-H), 5.76 (1H, s, 4-H).

In the same manner as above, (11β,18-epoxy-18α,21-dihydroxy-3,20-dioxo-4-pregnen-6β-ylthio)acetic acid (I: R¹=H; R²=β-SCH₂COOH) was also prepared from methyl (11β,18;18α,20α-bisepoxy-20β,21-isopropylidenedioxy-3-oxo-4-pregnen-6β-ylthio)acetate (II': R¹=H; R²=β-SCH₂COOCH₃; X=20,21(R)-acetonide) through (11β,18;18α,20α-bisepoxy-20β,21-isopropylidenedioxy-3-oxo-4-pregnen-6β-ylthio)acetic acid (II: R¹=H; R²=β-SCH₂COOH; X=20,21(R)-acetonide).

The compound (II: R¹=H; R²=β-SCH₂COOH; X=20,21(R)-acetonide) showed the following physical constants:

Elementary analysis for C₂₆H₃₄O₇S₄ (490.598): Calcd: C, 63.65%; H, 6.99%; S, 6.54%. Found: C, 63.90%; H, 6.76%; S, 6.46%.

M.P., 164°-166° C.

[α]_D²⁷+144.6±1.0 (c=1.010, chloroform).

UV λ_max^EtOH (nm, ε): 243 (13200).

IR ν_max^Nujol (cm⁻¹): 3300-3000, 2628, 1730, 1722, 1649, 1599, 1063, 886.

NMR (CDCl₃, δ): 1.40, 1.50, 1.54, (9H, 19-H and

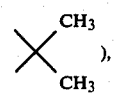

3.16 (2H, s, —SCH₂CO—), 3.88, 4.16 (2H, AB_q, J_AB=9 Hz, ν_ΔAB=16.8 Hz, 21—CH₂—), 4.81 (1H, d, J=6 Hz, 11-H), 5.31 (1H, s, 18-H), 5.81 (1H, s, 4-H).

Mass spectrum (MS m/z): 472 (M⁺−18, 1%), 414 (M⁺−76, 7%), 44 (100%).

REFERENCE EXAMPLE 1

Preparation of the starting materials used in Examples 1 and 2:

The compounds (II': R¹=SCH₂COOCH₃; R²=H; X=20,21(S)- or 20,21(R)-acetonide and R¹=H; R²=β-SCH₂COOCH₃; X=20,21(S)- or 20,21(R)-acetonide) used as the starting materials in Examples 1 and 2 were prepared in the following manner:

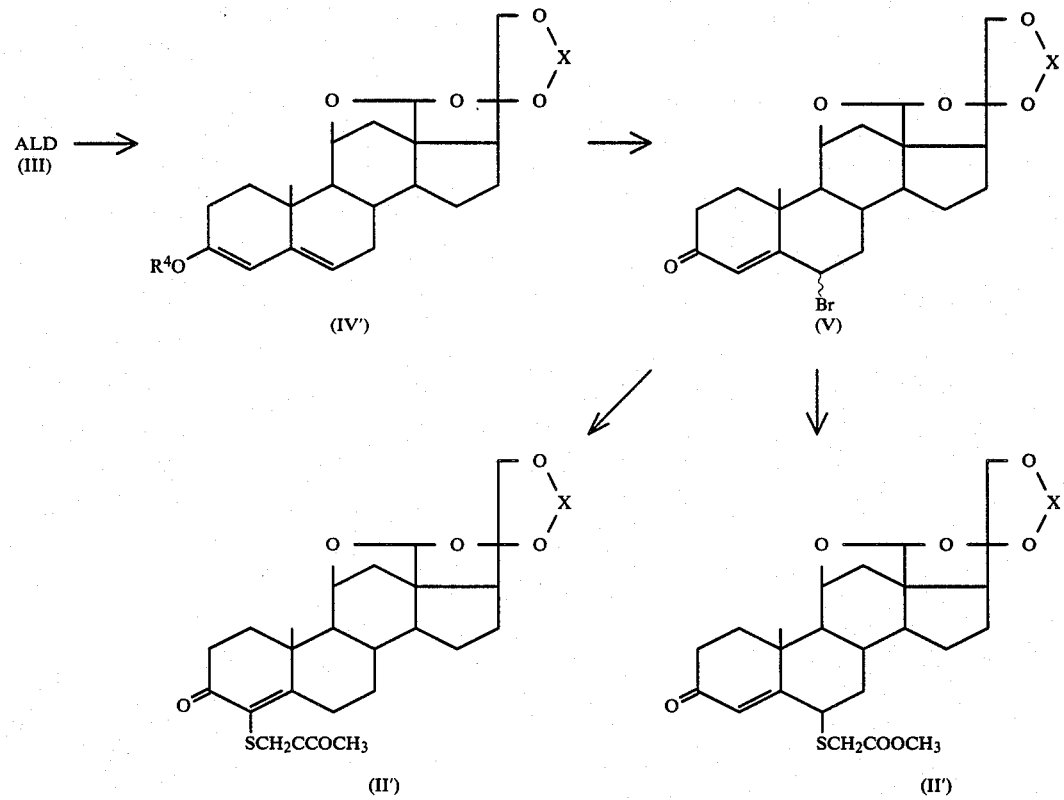

Namely, hemiacetal-type ALD (i.e. 11β,18-epoxy-18α,21-dihydroxy-4-pregnene-3,20-dione (III)) was reacted with 2,2-dimethoxypropane in the presence of p-toluenesulfonic acid in dimethylformamide to give 11β,18;18α,20β-bisepoxy-20α,21-isopropylidenedioxy-3-methoxy-3,5-pregnadiene (IV) (20,21(S)-acetonide)

and 11β,18;18α,20α-bisepoxy-20α,21-isopropylidenedioxy-3-methoxy-3,5-pregnadiene (IV) (20,21(R)-acetonide).

The compound (IV) (20,21(S)- or 20,21(R)-acetonides) was reacted with N-bromoacetamide to give 6β-bromo-11β,18;18α,20β-bisepoxy-20α,21-ispropylidenedioxy-4-pregnen-3-one (V: $R^1$=H; $R^2$=β-Br; X=20,21(S)-acetonide) or 6α-bromo-11β,18;18α,20β-bisepoxy-20α,21-isopropylidenedioxy-4-pregnen-3-one (V: $R^1$=H; $R^2$=β-Br; X=20,21(S)-acetonide) as well as 6β-bromo-11β,18;18α,20α-bisepoxy-20β,21-isopropylidenedioxy-4-pregnen-3-one (V: $R^1$=H; $R^2$=β-Br; X=20,21(R)-acetonide) or 6α-bromo-11β,18;18α,2-0α-bisepoxy-20β,21-isopropylidenedioxy-4-pregnen-3-one (V: $R^1$=H; $R^2$=α-Br; X=20,21(R)-acetonide).

These compounds were reacted, without isolation, with sodium methyl thioglycolate at room temperature to give the compounds (II': $R^1$=SCH$_2$COOCH$_3$; $R^2$=H; X=20,21(S)-and 20,21(R)-acetonides) as major products together with the compounds (II': $R^1$=H; $R^2$=β-SCH$_2$COOCH$_3$; X=20,21(S)-and 20,21(R)-acetonides) as minor products. The latter compounds were always 6β-isomers, and no 6α-isomer was obtained.

Physical values of the above intermediates were as follows:

Compound (II': $R^1$=SCH$_2$COOCH$_3$; $R^2$=H; X=20,21(S)-acetonide):

Elementary analysis for C$_{27}$H$_{36}$O$_7$S (504.624): Calcd.: C, 64.26%; H, 7.19%; S, 6.35%. Found: C, 64.09%; H, 7.07%; S, 6.07%.

M.P., 118°–120° C. (recrystallized from acetone/hexane).

$[α]_D^{24}$+169.3±2.1 (c=0.984, chloroform).

UV $λ_{max}^{EtOH}$ (nm, ε): 242 (11570).

IR $ν_{max}^{Nujol}$ (cm$^{-1}$): 1732, 1667, 1551, 1226, 1192, 1050, 1012, 990, 885, 815.

NMR (CDCl$_3$, δ) 100 MHz: 1.34, 1.49 (9H, 19-H and $$\times \begin{matrix} CH_3 \\ CH_3 \end{matrix} ),$$

3.36, 3.42 (2H, AB$_q$, $J_{AB}$=14 Hz, $ν_{ΔAB}$=5.9 Hz, SCH$_2$CO—), 3.64 (3H, s, —OCH$_3$) 3.90, 4.02 (2H, AB$_q$, $J_{AB}$=9 Hz, $ν_{ΔAB}$=12 Hz, 21—CH$_2$—), 4.86 (1H, d, J=6 Hz, 11-H), 5.30 (1H, s, 18-H).

Mass spectrum (MS m/z): 504 (M+, 1%), 446 (M+−58, 37%), 43 (100%).

Compound (II': $R^1$=H; $R^2$=β-SCH$_2$COOCH$_3$; X=20,21(S)-acetonide):

Elementary analysis for C$_{27}$H$_{36}$O$_7$S (504.624): Calcd.: C, 64.26%; H, 7.19%; S, 6.35%. Found: C, 64.90%; H, 7.37%; S, 7.15%.

M.P., 206°–208° C. (recrystallized from acetone/hexane).

$[α]_D^{24}$+210.3±3.2 (c=0.787, chloroform).

UV $λ_{max}^{EtOH}$ (nm, ε): 241 (15400).

IR $ν_{max}^{Nujol}$ (cm$^{-1}$): 1732, 1682, 1605, 1051, 1028, 1051, 1028, 999.

NMR (CDCl$_3$, δ) 100 MHz (the sample contained diethyl ether): 1.42, 1.49, 1.52 (9H, 19-H and $$\times \begin{matrix} CH_3 \\ CH_3 \end{matrix} ),$$

3.14 (2H, —SCH$_2$CO—), 3.72 (3H, s, —OCH$_3$) 3.92, 4.03 (2H, AB$_q$, $J_{AB}$=9 Hz, $ν_{ΔAB}$=11 Hz, 21—CH$_2$—), 4.83 (1H, d, J=6 Hz, 11-H), 5.34 (1H, s, 18-H), 5.70 (1H, s, 4-H).

Mass spectrum (MS m/z): 504 (M+, 80%), 446 (M+−58, 72%), 43 (100%).

Compound (II': $R^1$=SCH$_2$COOCH$_3$; $R^2$>H; X=20,21(R)-acetonide):

Elementary analysis for C$_{27}$H$_{36}$O$_7$S (504.624): Calcd: C, 64.26%; H, 7.19%; S, 6.35%. Found: C, 64.34%; H, 7.24%; S, 6.32%.

M.P., 140°–142° C. (recrystallized from acetone/hexane).

$[α]_D^{26}$+95.5±1.1 (c=1.034, chloroform).

UV $λ_{max}^{EtOH}$ (nm, ε): 241.5 (11760), 303 (2540).

IR $ν_{max}^{Nujol}$ (cm$^{-1}$): 1749, 1730, 1721, 1556, 1202, 1146, 1068, 1050, 1020, 997, 882.

NMR (CDCl$_3$, δ) 100 MHz: 1.35, 1.39, 1.49 (9H, 19-H and $$\times \begin{matrix} CH_3 \\ CH_3 \end{matrix} ),$$

3.36, 3.42 (2H, AB$_q$, $J_{AB}$=14 Hz, $ν_{ΔAB}$=6.1 Hz, —SCH$_2$CO—), 3.65 (3H, s, —OCH$_3$) 3.88, 4.16 (2H, AB$_q$, $J_{AB}$=9 Hz, $ν_{ΔAB}$=28 Hz, 21—CH$_2$—), 4.83 (1H, d, J=6 Hz, 11-H), 5.28 (1H, s, 18-H).

Mass spectrum (MS m/z): 504 (M+, 62%), 72 (100%).

Compound (II': $R^1$=H; $R^2$=β-SCH$_2$COOCH$_3$; X=20,21(R)-acetonide):

Elementary analysis for C$_{27}$H$_{36}$O$_7$S (504.624): Calcd: C, 64.26%; H, 7.19%; S, 6.35%. Found: C, 64.53%; H, 7.19%; S, 6.61%.

M.P., 192°–194° C. (recrystallized from acetone/hexane).

$[α]_D^{24}$+150.1±1.9 (c=1.997, chloroform).

UV $λ_{max}^{EtOH}$ (nm, ε): 241.5 (15300).

IR $ν_{max}^{Nujol}$ (cm$^{-1}$): 1726, 1682, 1607, 1160, 1077, 1063, 1023.

NMR (CDCl$_3$, δ) 100 MHz: 1.39, 1.49, 1.53 (9H, 19-H and $$\times \begin{matrix} CH_3 \\ CH_3 \end{matrix} ),$$

3.10, 3.19 (2H, AB$_q$, $J_{AB}$=15 Hz, $ν_{ΔAB}$=9.1 Hz, —SCH$_2$CO—), 3.73 (3H, s, —OCH$_3$), 3.86, 4.16 (2H, AB$_q$, $J_{AB}$=9 Hz, $ν_{ΔAB}$=28 Hz, 21—CH$_2$—), 4.81 (1H, d, J=6 Hz, 11-H), 5.30 (1H, s, 18-H), 5.71 (1H, s, 4-H).

Compound (IV) (20,21(S) acetonide):

Elementary analysis for C$_{25}$H$_{34}$O$_5$ (414.522): Calcd.: C, 72.43%; H, 8.27%. Found: C, 72.39%; H, 8.31%.

M.P., 164°–168° C. (recrystallized from acetone/hexane).

$[α]_D^{26}$−32.4±1.0 (c=0.701, chloroform).

UV $λ_{max}^{EtOH}$ (nm, ε): 240.5 (19500).

IR $\nu_{max}^{Nujol}$ (cm$^{-1}$): 1650, 1625, 1246, 1236, 1168, 1048, 1020, 996.

NMR (CDCl$_3$, δ): 1.08, 1.34, 1.51 (9H, 19-H and

), 3.58 (3H, s, —OCH$_3$), 3.88, 4.04 (2H, AB$_q$, J$_{AB}$=9 Hz, $\nu_{\Delta AB}$=6.3 Hz, 21—CH$_2$—), 4.90 (1H, d, J=6 Hz, 11-H), 5.14 (2H, 4-H and 6-H), 5.33 (1H, s, 18-H).

Compound (IV) (20,21(R)-acetonide):

Elementary analysis for C$_{25}$H$_{34}$O$_5$ (414.522): Calcd: C, 72.43%; H, 8.27%. Found: C, 72.38%; H, 8.27%.

M.P., 126°–129° C. (recrystallized from dichloromethane/methanol).

[α]$_D^{26}$ −86.1±2.0 (c=0.634, chloroform).

UV λ$_{max}^{EtOH}$ (nm, ε): 240.5 (19150).

IR $\nu_{max}^{Nujol}$ (cm$^{-1}$): 1648, 1622, 1233, 1180, 1168, 1071, 1053, 989, 725.

NMR (CDCl$_3$, δ): 1.09, 1.40, 1.50 (9H, 19-H and

), 3.59 (3H, s, —OCH$_3$), 3.90, 4.20 (2H, AB$_q$, J$_{AB}$=9 Hz, $\nu_{\Delta AB}$=17.9 Hz, 21—CH$_2$—), 4.90 (1H, d, J=6 Hz, 11-H), 5.15 (2H, 4-H and 6-H), 5.30 (1H, s, 18-H).

Compound (V: R$^1$=H; R$^2$=β-Br; X=20,21(S)-acetonide):

NMR (CDCl$_3$, δ): 1.34, 1.64 (9H, 19-H and

), 3.94, 4.04 (2H, AB$_q$, J$_{AB}$=9 Hz, $\nu_{\Delta AB}$=6.3 Hz, 21—CH$_2$—), 4.99 (1H, eq-H, 6α-H), 4.86 (1H, d, J=6 Hz, 11-H), 5.44 (1H, s, 18-H), 5.92 (1H, s, 4-H).

Compound (V: R$^1$=H; R$^2$=α-Br; X=20,21(S)-acetonide):

NMR (CDCl$_3$, δ): 1.33, 1.49 (9H, 19-H and

), 3.94, 4.05 (2H, AB$_q$, J$_{AB}$=9 Hz, $\nu_{\Delta AB}$=6.3 Hz, 4.87 (1H, m, ax-H, 6β-H), 4.83 (1H, d, J=6 Hz, 11-H), 5.27 (1H, s, 18-H), 6.44 (1H, d, J=2 Hz, 4-H).

Compound (V: R$^1$=H; R$^2$=β-Br; X=20,21(R)-acetonide):

NMR (CDCl$_3$, δ): 1.39, 1.65 (9H, 19-H and

), 3.89, 4.17 (2H, AB$_q$, J$_{AB}$=9 Hz, $\nu_{\Delta AB}$=16.8 Hz, 21—CH$_2$—), 4.97 (1H, m, eq-H, 6α-H), 4.83 (1H, d, J=6 Hz, 11-H), 5.38 (1H, s, 18-H), 5.91 (1H, s, 4-H).

Compound (V: R$^1$=H; R$^2$=α-Br; X=20,21(R)-acetonide):

NMR (CDCl$_3$, δ): 1.42, 1.50 (9H, 19-H and

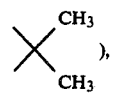

), 3.90, 4.18 (2H, AB$_q$, J$_{AB}$=9 Hz, $\nu_{\Delta AB}$=16.7 Hz, 21—CH$_2$—), 4.92 (1H, m, ax-H, 6β-H), 4.82 (1H, d, J=6 Hz, 11-H), 5.28 (1H, s, 18-H), 6.41 (1H, d, J=2 Hz, 4-H).

EXAMPLE 3-1

Preparation of N-(p-hydroxyphenethyl)-2-(11β,18-epoxy-18α,21-dihydroxy-3,20-dioxo-4-pregnen-4-ylthio)-acetamide (I:

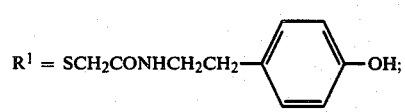

R$^2$=H):

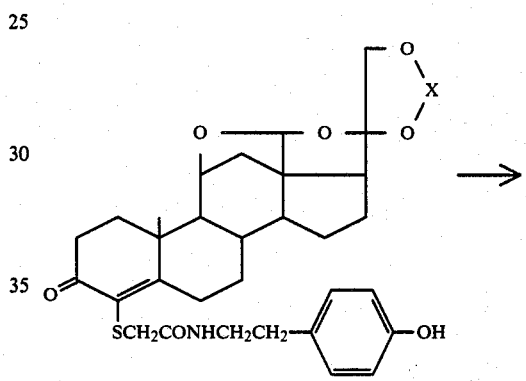

(II)

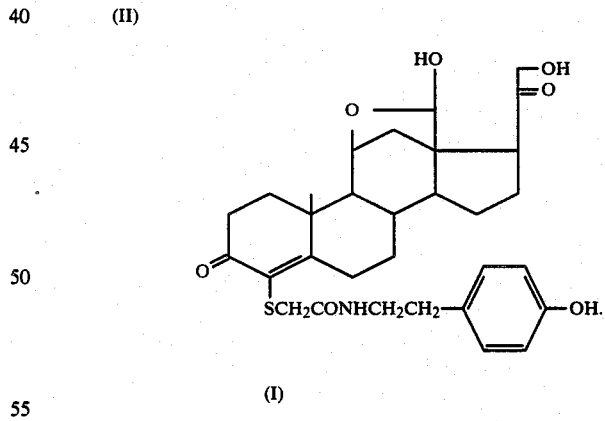

(I)

To N-(p-hydroxyphenethyl)-2-(11β,18;18α,20β-bisepoxy-20α,21-isopropylidenedioxy-3-oxo-4-pregnen-4-ylthio)acetamide (II:

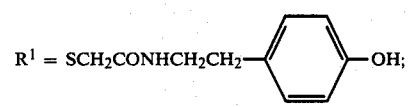

R$^2$=H; X=20,21(S)-acetonide) (27 mg) was added 70% acetic acid (3 ml), and reaction was carried out in nitrogen stream at room temperature for 5 hours. The reaction mixture was combined with ice-water and extracted with ethyl acetate. The extract was washed repeatedly with an aqueous sodium chloride solution, dried over anhydrous sodium sulfate and concentrated under reduced pressure. The residue was dissolved in methanol and treated with activated charcoal. Thereafter, ether was added thereto, and the deposited powder was collected by filtration to give N-(p-hydroxyphenethyl)-2-(11β,18-epoxy-18,21-dihydroxy-3,20-dioxo-4-pregnen-4-ylthio)acetamide (I:

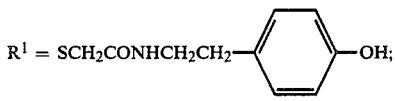

$R^2=H$) (21 mg).

Softening point: 114°–117° C.

NMR (d$_6$-acetone, δ): 1.22, 1.30, 1.35 (3H, 19-H), 4.54, 4.78 (1H, each, d, J=6 Hz, 11-H), 5.06, 5.40 (1H, each, s, 18-H), 6.77, 7.05 (4H, A$_2$B$_{2q}$, J$_{AB}$=8 Hz, ν$_{ΔAB}$=17 Hz,

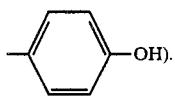

NMR (CD$_3$OD, δ): 1.23, 1.34 (3H, 19-H), 5.03, 5.45 (1H, each, s, 18-H), 6.74, 7.05 (4H, A$_2$B$_{2q}$, J$_{AB}$=8 Hz, ν$_{ΔAB}$=18.4 Hz,

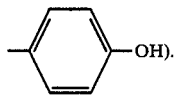

UV λ$_{max}^{EtOH}$ (nm, ε): 225.5 (13800), 242 (8900), 279 (3000), 285.5 (3000), 299 (2300).

TLC: Rf=0.32 (dichloromethane/acetone=1/1). In the same manner as above, the said compound (I) was also prepared from N-(p-hydroxyphenethyl)-2-(11β,18;18α,20β-bisepoxy-20α,21-isopropylidenedioxy-3-oxo-4-pregnen-4-ylthio)acetamide (II:

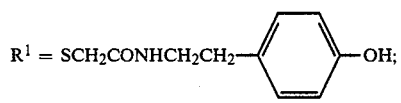

$R^2=H$; X=20,21(R)-acetonide).

EXAMPLE 3-2

Preparation of N-(p-hydroxy-α-methoxycarbonylphenethyl)-2-(11β,18-epoxy-18α,21-dihydroxy-3,20-dioxo-4-pregnen-4-ylthio)acetamide (I:

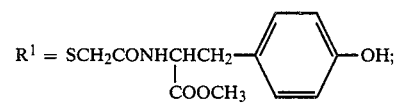

$R^2=H$):

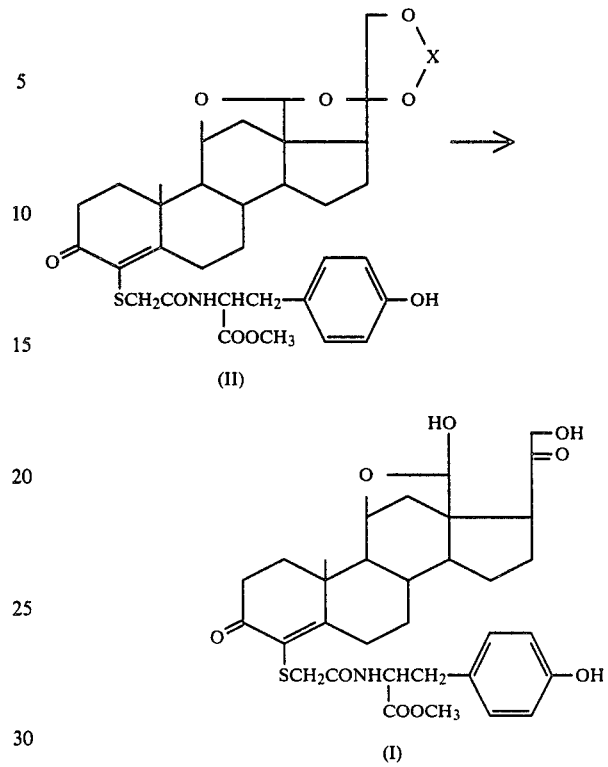

To N-(p-hydroxy-α-methoxycarbonylphenethyl)-2-(11β,18;18α,20β-bisepoxy-20α,21-isopropylidenedioxy-3-oxo-4-pregren-4-ylthio)acetamide (II) (20,21(R)-acetonide) (27 mg) was added 70% acetic acid (2 ml), and reaction was carried out in nitrogen stream at room temperature for 7 hours. The reaction mixture was combined with ice-water and extracted with ethyl acetate. The extract was washed with an aqueous saturated sodium chloride solution, dried over anhydrous sodium sulfate and concentrated under reduced pressure. The residue was subjected to reversed-phase chromatography (Merck, Lover column, RP-8, size B; eluent: 65% aqueous methanol). Ether was added to the major fraction. The deposited powder was collected by filtration to give N-(p-hydroxy-α-methoxycarbonylphenethyl)-2-(11β,18-epoxy-18α,21-dihydroxy-3,20-dioxo-4-pregnen-4-ylthio)acetamide (I:

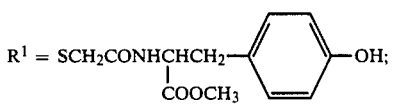

$R^2=H$) (18 mg). Yield, 70.9%.

NMR (d$_6$-acetone, δ): 1.23, 1.33 (3H, 19-H), 3.31 (2H, s, —SCH$_2$CO), 3.65 (3H, s, —COOCH$_3$), 4.51 (1H, m, NHCHCOO—). 4.56, 4.77 (1H, each, d, 11-H), 5.06, 5.40 (1H, each, s, 18-H), 6.77, 7.06 (4H, A$_2$B$_{2q}$, J$_{AB}$=8 Hz, ν$_{ΔAB}$=17.2 Hz,

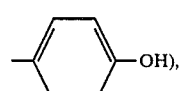

7.63 (1H, d, J=7.5 Hz, —CONH).

Mass spectrum (MS m/z): 627 (M+, 1%), 178 (100%).

TLC: Rf=0.19 (chloroform/acetone=1/1), 0.33 (chloroform/methanol=9/1).

EXAMPLE 3-3

Preparation of N-[2-(1H-imidazol-4-yl)ethyl]-2-(11β,18-epoxy-18α,21-dihydroxy-3,20-dioxo-4-pregnen-4-ylthio)acetamide (I:

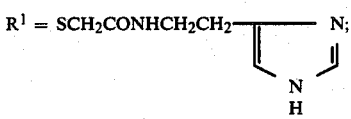

$R^2$=H):

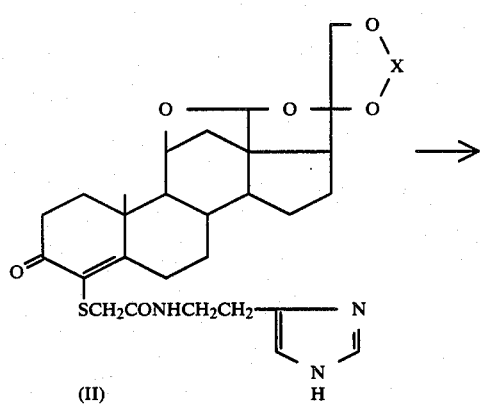

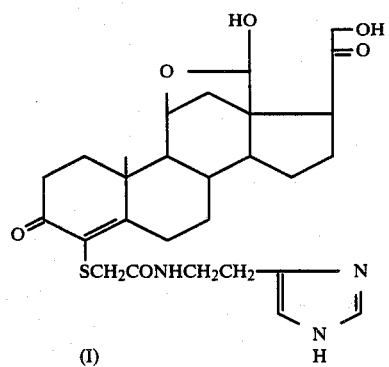

To N-[2-(1H-imidazol-4-yl)ethyl]-2-(11β,18;18α,20β-bisepoxy-20α,21-isopropylidenedioxy-3-oxo-4-pregnen-4-ylthio)acetamide (II) (20,21(R)-acetonide) (12 mg) was added 70% acetic acid (1 ml), and reaction was carried out in nitrogen stream at room temperature for 6.5 hours. The reaction mixture was treated in the same manner as in Example 3-2 to give N-[2-(1H-imidazol-4-yl)ethyl]-2-(11β,18-epoxy-18α,21-dihydroxy-3,20-dioxo-4-pregnen-4-ylthio)acetamide (I:

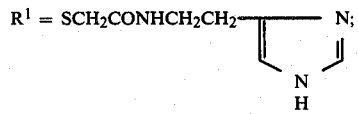

$R^2$=H) as powders.

Yield, 53.7%. Softening point, 87° C.

NMR (d$_6$-acetone, δ): 1.22, 1.33 (2H, 19-H), 4.55, 4.77 (1H, each, d, 11-H), 5.06, 5.41 (1H, each, s, 18-H), 6.85, 7.62 (2H, each, broad s,

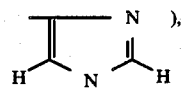

7.55 (1H, —NH—).

Mass spectrum (MS m/z): 543 (M+, 1%), 94 (100%).

TLC: Rf=0.19 (chloroform/methanol=5/1).

REFERENCE EXAMPLE 2-1

Preparation of the starting materials used in Example 3-1:

The starting compound (II: $R^1$=

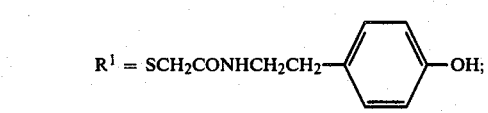

$R^2$=H; X=20,21(S)- or 20,21(R)-acetonide) was prepared by demethylating the compound (II: $R^1$=SCH$_2$COOCH$_3$; $R^2$=H; X=20,21(S)- or 20,21(R)-acetonide) as in Reference Example 1 and reacting the resultant carboxylic acid with tyramine in the presence of 1-hydroxybenzotriazole and dicyclohexylcarbodiimide in tetrahydrofuran under ice-cooling [W. König et al.: Chem.Ber. 103, 788 (1970)].

Compound (II:

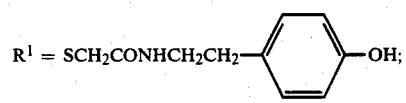

$R^2$=H; X=20,21(S)-acetonide) (oily substance):
NMR (CDCl$_3$, δ): 1.26, 1.30, 1.34, 1.50 (9H, 19-H and

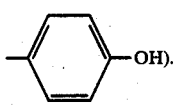

3.91, 4.20 (2H, AB$_q$, J$_{AB}$=9 Hz, ν$_{ΔAB}$=6.3 Hz, 21-CH$_2$—), 4.83 (1H, d, J=6 Hz, 11-H), 5.31 (1H, s, 18-H), 6.74, 7.02 (4H, A$_2$B$_{2q}$, J$_{AB}$=8 Hz, ν$_{ΔAB}$=16.4 Hz,

—OH).

Compound (II:

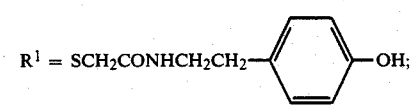

$R^2$=H; X=20,21(R)-acetonide):
NMR (CDCl$_3$, δ): 1.31, 1.39, 1.49 (9H, 19-H and

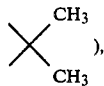

3.89, 4.17 (2H, AB$_q$, J$_{AB}$=9 Hz, ν$_{\Delta AB}$=17.2 Hz, 21-CH$_2$—), 4.81 (1H, d, J=6 Hz, 11-H), 5.29 (1H, s, 18-H), 6.76, 7.03 (4H, A$_2$B$_{2q}$, J$_{AB}$=8 Hz, ν$_{\Delta AB}$=16.6 Hz,

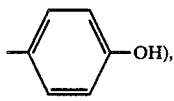

7.58 (1H, t-like, —NH).

Mass spectrum (MS m/z): 609 (M$^+$, 3%), 594 (M$^+$, —15, 3%), 120 (100%).

TLC: Rf=0.30 (ethyl acetate/benzene=4/1), 0.41 (chloroform/acetone=3/1).

REFERENCE EXAMPLE 2-2

Preparation of the starting material used in Example 3-2:

The starting compounds (II:

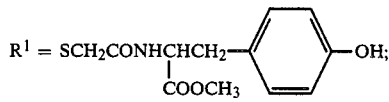

R$^2$=H; X=20,21(S)- and 20,21(R)-acetonide) used in Example 3-2 was obtained in the same manner as in Reference Example 2-1 but using the compound (II': R$^1$=SCH$_2$COOCH$_3$; R$^2$=H; X=20,21(S)- or 20,21(R)-acetonide). In case of the 20,21(R)-acetonide, the objective compound (28 mg) was obtained as powders (28 mg) from the ester (35 mg). Yield, 60.5%.

20,21(R)-acetonide: Softening point, 108° C.
NMR (CDCl$_3$, δ): 1.26, 1.31, 1.40, 1.49 (19-H and

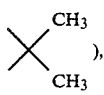

3.26 (2H, s, —SCH$_2$CO—), 3.66 (3H, S, —COOCH$_3$) 3.85, 4.13 (2H, AB$_q$, J$_{AB}$=9 Hz, ν$_{\Delta AB}$=9 Hz, ν$_{\Delta AB}$=1.66 Hz, 21-CH$_2$—), 4.63 (1H, m, —NHCHCOOCH$_3$), 4.78 (1H, d, J=6 Hz, 11-H), 5.24 (1H, s, 18-H), 6.66, 6.96 (4H, A$_2$B$_{2q}$, J$_{AB}$=8.5 Hz, ν$_{\Delta AB}$=17.7 Hz,

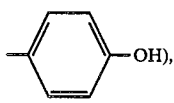

7.64 (1H, d, J=7.5 Hz, —CONH—).

IR ν$_{max}^{CHCl_3}$ (cm$^{-1}$): 3584, 3280 (broad), 1745, 1672, 1613, 1594.

Mass spectrum (MS m/z): 667 (M$^+$, 2%), 107 (100%).

TLC: Rf=0.41 (chloroform/acetone=3/1).

REFERENCE EXAMPLE 2-3

Preparation of the starting materials used in Example 3-3:

The starting compound (II:

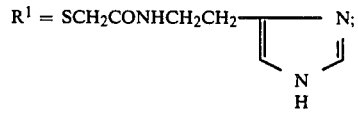

R$^2$=H; X=20,21(S)- or 20,21(R)-acetonide) used in Example 3-3 was obtained in the same manner as in Reference Example 2-1 but using the compound (II': R$^1$=SCH$_2$COOCH$_3$; R$^2$=H; X=20,21(S)- or 20,21(R)-acetonide). But, the corresponding intermediate carboxylic acid obtained from 22 mg of the methyl ester (20,21(R)-acetonide) was dissolved in dimethylformamide (2 ml) in place of tetrahydrofuran and reacted with histamine hydrochloride (9 mg, 1.1 mol) in the presence of N-methylmorpholine (15.4 μl, 3.5 mol), 1-hydroxybenzotriazole (6.5 mg, 1.1 mol) and dicyclohexylcarbodiimide (11.7 mg, 1.3 mol) while ice-cooling for 17 hours. After the reaction was over, the solvent was removed under reduced pressure, and the residue was subjected to reversed-phase chromatography (Merck, Lover column, size A). Ether was added to the major fraction. The deposited powder was collected by filtration to give the objective compound (II) (13 mg). Yield, 51.1%.

20,21(R) acetonide: Softening point, 122°–124° C.
NMR (CDCl$_3$, δ): 1.30, 1.39, 1.49 (19-H and

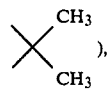

3.87, 4.15 (2H, AB$_q$, J$_{AB}$=9 Hz, ν$_{\Delta AB}$=16.8 Hz, 21-CH$_2$—), 4.80 (1H, d, J=6 Hz, 11-H), 5.27 (1H, s, 18-H), 6.81, 7.55 (2H, each, broad s,

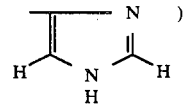

6.41, 7.92 (2H, —NH—).

Mass spectrum (MS m/z): 583 (M$^+$, 1%), 94 (100%).

TLC: Rf=0.39 (chloroform/methanol=6/1).

EXAMPLE 4

Preparation of immunogen and antiserum with the compound (I: R$^1$=SCH$_2$COOH; R$^2$=H):

(1) IMMUNOGEN

An activated ester solution was prepared by adding tributylamine (9.3 μl) and isobutyl chloroformate (4.9 μl) to a solution of the compound (I: R$^1$=SCH$_2$COOH; R$^2$=H) (18 mg) in dioxane (500 μl) kept at 10°–20° C. and stirring the resultant mixture for 30 minutes.

Separately, dioxane (2 ml) was added to a solution of bovine serum albumin (BSA) (69 mg) in water (2 ml), and the mixture was adjusted to pH 8.5 with 1N aqueous sodium hydroxide. To this solution was added dropwise the activated ester solution obtained above while ice-cooling. The mixture was stirred for 4 hours keeping the pH value at 8.5 to accomplish coupling, dialyzed with water and lyophilized to give a BSA conjugate of the compound (I) (50 mg). The molar ratio of the combined hapten to the carrier protein was 15.

(2) ANTISERUM

The immunogen (250 μg) obtained above was dissolved in physiological saline solution (250 μl), and Freund's complete adjuvant (250 μl) was added thereto to make an emulsion. The emulsion was injected subcutaneously to rabbits at the dorsal part. The injection was repeated 5 times at three-week intervals. Ten days after the final immunization, the whole blood was drawn from the rabbits to obtain antiserum.

The titer of the antiserum was determined with an RIA system as hereinafter described and represented by the dilution fold of antiserum required to combine 50% of $^{125}$I-labelled ALD $2.2 \times 10^4$ dpm. The result was $4.5 \times 10^4$ fold.

EXAMPLE 5-1

Labelling of the compound (I:

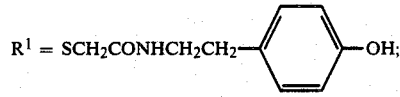

$R^2=H$):

A mixture of the compound (I:

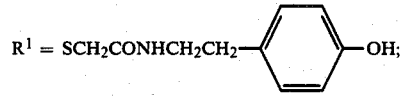

$R^2=H$) (500 μg) prepared in Example 3-1, dimethylformamide (5 μl), 0.5M-phosphate buffer (pH, 7.5) (25 μl) and $^{125}$I-sodium iodide (1 mCi) was admitted into a glass tube. A phosphate buffer (pH, 7.5) (5 μl) containing Chloramine-T (sodium paratoluenesulfochloramine) (20 μg) was added thereto. After stirring at room temperature for 45 seconds, an aqueous solution (5 μl) containing sodium metabisulfite (100 μg) was added thereto to stop the reaction. Potassium iodide (500 μg) was added to the reaction mixture, which was then extracted with dichloromethane (1 ml). The extract was dried over anhydrous sodium sulfate and chromatographed (Sephadex LH-20, 0.7 cmφ×20 cm, dichloromethane/methanol=9/1) to give the labelled product having a radioactivity of 1000–1500 μCi/μg. The chromatogram (elution curve) is shown in FIG. 1 of the accompanying drawings.

EXAMPLE 5-2

Labelling of the compounds (I:

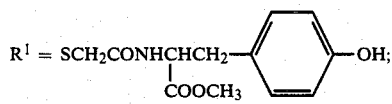

$R^2=H$) and (I:

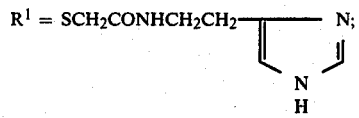

Figure 2:
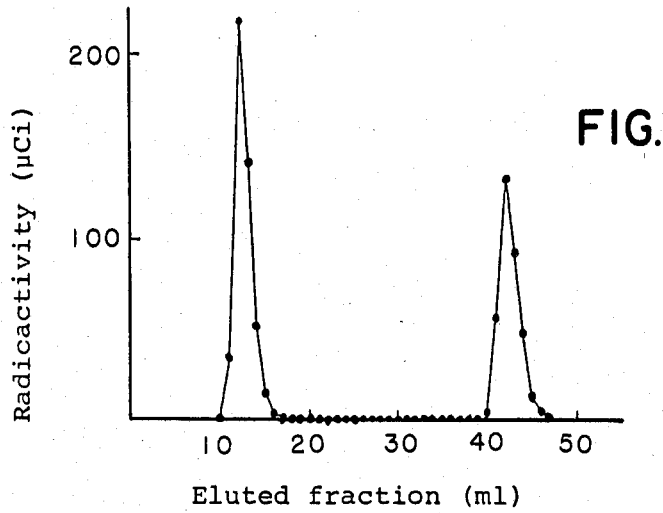
Figure 3:
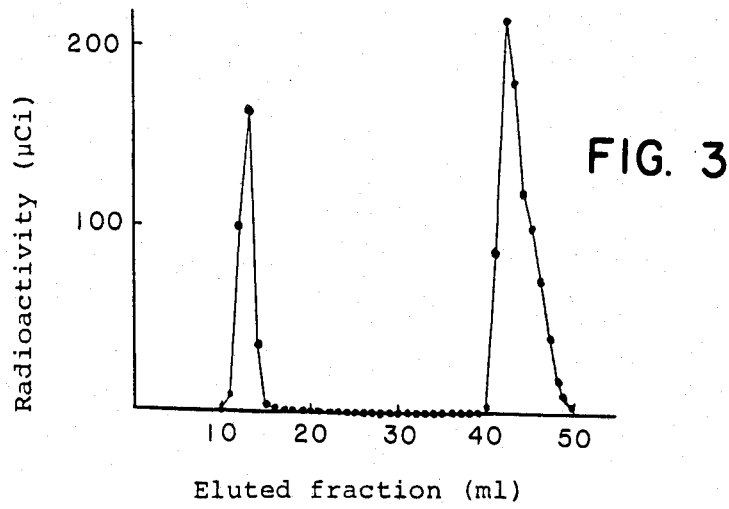

$R^2=H$):

In the same manner as in Example 5-1, the compounds (I) as obtained in Examples 3-2 and 3-3 were labelled. Each of the labelled products was purified by chromatography (Sephadex LH-20, 9 mmφ×90 mm, ethanol-M/10 citrate buffer) to give the tyrosine methyl ester product having a radioactivity of 500 μCi/μg or the histamine product having a radioactivity of 400 μCi/μg. The chromatograms (elution curves) are shown in FIGS. 2 and 3 of the accompanying drawings.

EXAMPLE 6

Preparation of 11β,18-epoxy-18α,21-dihydroxy-3,20-dioxo-4-pregnen-6β-yl hemisuccinate (I: $R^1=H$; $R^2=\beta$-OCOCH$_2$CH$_2$COOH):

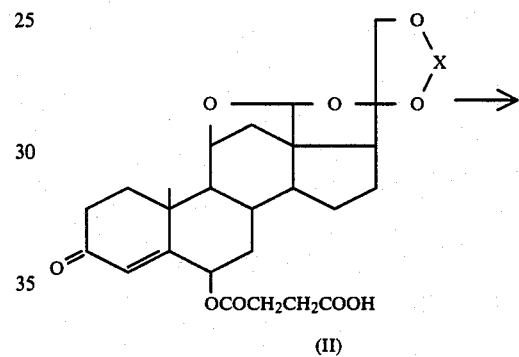

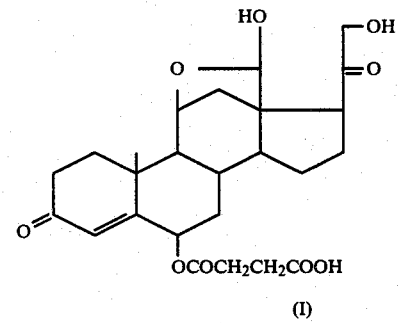

A solution of 11β,18;18α,20β-bisepoxy-20α,21-isopropylidenedioxy-3-oxo-4-pregnen-6β-yl hemisuccinate (II: $R^1=H$; $R^2=\beta$-OCOCH$_2$CH$_2$COOH; X=20,21(S)-acetonide) (35 mg) in 70% acetic acid (4 ml) was stirred in nitrogen stream at room temperature for 16 hours. The resultant mixture was admixed water and extracted with ethyl acetate. The extract was washed with an aqueous sodium chloride solution, dried over anhydrous sodium sulfate and concentrated under reduced pressure. The residue was dissolved in methanol and treated with activated charcoal. Ether was added to the metanolic solution. The deposited powder was collected by filtration to give 11β,18-epoxy-18α,21-dihydroxy-3,20-dioxo-4-pregnen-6β-yl hemisuccinate (I: $R^1=H$; $R^2=\beta$-OCOCH$_2$CH$_2$COOH) (16 mg). Yield, 49.6%.

Elementary analysis for C25H32O9.½H2O (485.514): Calcd.: C, 61.84%; H, 6.85%. Found: C, 62.09%; H, 7.30%.

Mass spectrum (MS m/z): 458 (M+ −18, 2%), 429 (M+ −47, 11%), 358 (M+ −118, 57%), 149 (100%).

NMR (CDCl3, δ): 1.28, 1.39 (3H, 19-H), 2.66 (4H, s,

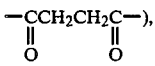

5.33 (1H, s, 18-H), 5.45 (1H, w½=8 Hz, 6α-H), 5.94 (1H, s, 4-H).

TLC: Rf=0.17 (ethyl acetate/cyclohexane/acetic acid/ethanol=20/10/1/2).

In the same manner as above, the said compound (I) was also obtained by the use of the compound (II: R¹=H; R²=β-OCOCH2CH2COOH; X=20,21(R)-acetonide) (79 mg) in place of the compound (II: R¹=H; R²=β-OCOCH2CH2COOH; X=20,21(S)-acetonide).

EXAMPLE 7

Preparation of 11β,18-epoxy-18α,21-dihydroxy-3,20-dioxo-4-pregnen-6β-yl hemisuccinate (I: R¹=H; R²=α-OCOCH2CH2COOH):

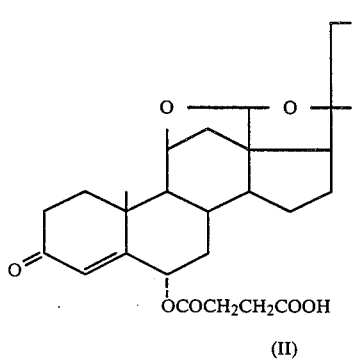

(II)

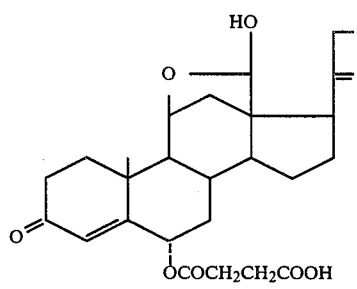

(I)

In the same manner as in Example 6, the objective compound (I: R¹=H; R²=α-OCOCH2CH2COOH) (10mg) was obtained from 11β,18;18α,20β-bisepoxy-20α,21-isopropylidenedioxy-3-oxo-4-pregnen-6α-yl hemisuccinate (II: R¹=H; R² =α-OCOCH2CH2COOH; X=20,21(S)-acetonide) (23 mg). Yield, 47.1%.

Elementary analysis for C25H32O9.2H2O (512.538): Calcd.: C, 58.58%; H, 7.08%. Found: C, 57.99%; H, 6.78%.

Mass spectrum (MS m/z): 458 (M+ −18, <1%), 429 (M+ −47, 20%), 358 (M+ −118, 57%), 28 (100%).

NMR (CDCl3, δ): 1.27 (19-H), 2.70, 2.67 C4H, SH

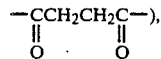

5.32 (1H, s, 18-H), 5.94 (1H, d, J=2 Hz, 4-H).

TLC: Rf=0.17 (ethyl acetate/cyclohexane/ethanol/acetic acid=20/10/2/1).

In the same manner as above, the said compound (I) was also obtained from 11β,18;18α,20α-bisepoxy-20β,21-isopropylidenedioxy-3-oxo-4-pregnen-6α-yl hemisuccinate (II: R¹=H; R²=α-OCOCH2CH2COOH; X=20,21(R)-acetonide) (49 mg).

REFERENCE EXAMPLE 3

Preparation of the starting materials used in Examples 6 and 7:

The compounds (II: R¹=H; R²=β-OCOCH2CH2COOH; X=20,21(S)- or 20,21(R)-acetonide) and (II: R¹=H; R²=α-OCOCH2CH2COOH; X=20,21(S)- or 20,21(R)-acetonide) used as the starting materials in Examples 6 and 7 were prepared from the compound (IV) (20,21(S)- or 20,21(R)-acetonide) as described in Reference Example 1 in the following manner:

(IV) 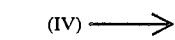

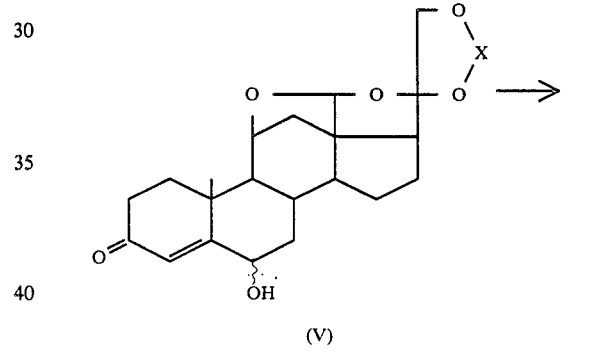

(V)

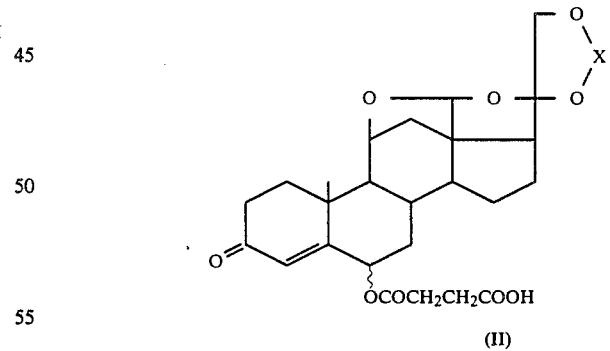

(II)

The compound (IV) (20,21(S)- or 20,21(R)-acetonide) was dissolved in 10% aqueous tetrahydrofuran and reacted with m-chloroperbenzoic acid with stirring and ice-cooling. The reaction product was chromatographed to give 11β,18;18α,20β-bisepoxy-6β-hydroxy-20α,21-isopropylidenedioxy-4-pregnen-3-one (V: R¹=H; R²=β-OH; X=20,21(S)-acetonide) and 11β,18;18α,20β-bisepoxy-6α-hydroxy-20α,21-isopropylidenedioxy-4-pregnen-3-one (V: R¹=H; R²=α-OH; X=20,21(S)-acetonide) as well as 11β,18;18α,20α-bisepoxy-6β-hydroxy-20β,21-isopropylidenedioxy-4- pregnen-3-one (V: R¹=H; R²=β-OH; X=20,21(R)-acetonide) and 11β,18;18α,20α-bisepoxy-6α-hydroxy-20β,21-isopropylidenedioxy-4-pregnen-3-one (V: R¹=H; R²=α-OH; X=20,21(R)-acetonide).

Compound (V: R¹=H; R²=β-OH; X=20,21(S)-acetonide):
Elementary analysis for C$_{24}$H$_{32}$O$_6$ (416.496): Calcd. C, 69.32%; H, 7.75%. Found: C, 68.84%; H, 7.63%.
M.P., 242°–245° C. (recrystallized from acetone/hexane).
Mass spectrum (MS m/z): 416 (M+, 29%), 401 (M+ −15, 64%), 72 (100%).
NMR (CDCl$_3$, δ): 1.35, 1.48 (9H, 19-H,

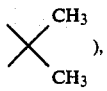

3.83, 4.03 (2H, AB$_q$, J$_{AB}$=8.8 Hz, ν$_{ΔAB}$=6.2 Hz, 21-CH$_2$—), 4.28 (1H, w½=8 Hz, 6α-H), 4.76 (1H, d, J=6 Hz, 11-H), 5.32 (1H, s, 18-H), 5.76 (1H, s, 4-H).
[α]$_D^{20}$: +110.9±1.5 (c=1.008, chloroform).

Compound (V: R¹=H; R²=α-OH: X=20,21(S)-acetonide):
Elementary analysis for C$_{24}$H$_{32}$O$_6$ (416.496): Calcd.: C, 69.32%; H, 7.75%. Found: C, 68.78%; H, 7.62%.
M.P., 245°–248° C. (recrystallized from acetone/hexane).
Mass spectrum (MS m/z): 416 (M+, 21%), 401 (M+ −15, 47%), 72 (100%).
NMR (CDCl$_3$, δ): 1.28, 1.35, 1.49 (9H, 19-H,

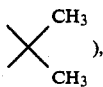

3.88, 3.98 (2H, AB$_q$, J$_{AB}$=8.8 Hz, ν$_{ΔAB}$=6.3 Hz, 21-CH$_2$—), 4.27 (1H, m, 6β-H), 4.80 (1H, d, J=6 Hz, 11-H), 5.25 (1H, s, 18-H), 6.14 (1H, d, J=2 Hz, 4-H).

Compound (V: R¹=H; R²=β-OH: X=20,21(R)-acetonide):
Elementary analysis for C$_{24}$H$_{32}$O$_6$ (416.496): Calcd.: C, 69.32%; H, 7.75%. Found: C, 69.22%; H, 7.65%.
M.P., 238°–241° C. (recrystallized from acetone/hexane).
Mass spectrum (MS m/z): 416 (M+, 92%), 401 (M+ −15, 46%), 72 (100%).
NMR (CDCl$_3$, δ): 1.40, 1.50 (9H, 19-H,

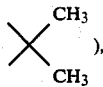

3.86, 4.14 (2H, AB$_q$, J$_{AB}$=9 Hz, ν$_{ΔAB}$=16.6 Hz, 21-CH$_2$—), 4.31 (1H, w½=8 Hz, 6α-H), 4.76 (1H, d, J=6 Hz, 11-H), 5.30 (1H, s, 18-H), 5.72 (1H, s, 4-H), [α]$_D^{20}$: +39.8±0.8 (c=1.002, chloroform).

Compound (V: R¹=H; R²=α-OH: X=20,21(R) acetonide):
Elementary analysis for C$_{24}$H$_{32}$O$_6$ (416.496): Calcd.: C, 69.21%; H, 7.75%. Found: C, 68.96%; H, 7.76%.
M.P., 192°–194° C. (recrystallized from acetone/hexane).
Mass spectrum (MS m/z): 416 (M+, 45%), 401 (M+ −15, 29%), 72 (100%).

NMR (CDCl$_3$, δ): 1.28, 1.39, 1.48 (9H, 19-H,

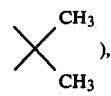

3.83, 4.12 (2H, AB$_q$, J$_{AB}$=9 Hz, ν$_{ΔAB}$=16.7 Hz, 21-CH$_2$—), 4.27 (1H, m, 6β-H), 4.77 (1H, d, J=6 Hz, 11-H), 5.22 (1H, s, 18-H), 6.14 (1H, d, J=2 Hz, 4-H), [α]$_D^{20}$: +95.1±1.3 (c=1.012, chloroform).

Then, the compound (V) was dissolved in pyridine and reacted with succinic anhydride in the presence of 4-dimethylaminopyridine with warming to give the compound (II: R¹=H; R²=β-OCOCH$_2$CH$_2$COOH; X=20,21(S)- or 20,21(R)-acetonide) or (II: R¹=H; R²=α-OCOCH$_2$CH$_2$COOH; X=20,21(S)- or 20,21(R)-acetonide).

Compound (II: R¹=H; R²=β-OCOCH$_2$CH$_2$COOH: X=20,21(S)-acetonide):
M.P., 211°–213° C.
NMR (CDCl$_3$, δ): 1.36, 1.41, 1.52 (9H, 19-H,

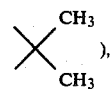

2.67 (4H, s, $$-\underset{O}{\underset{\|}{C}}CH_2CH_2\underset{O}{\underset{\|}{C}}-),$$

3.94, 4.05 (2H, AB$_q$, J$_{AB}$=9 Hz, ν$_{ΔAB}$=6.3 Hz, 21-CH$_2$—), 4.87 (1H, d, J=6 Hz, 11-H), 5.40 (1H, s, 18-H), 5.44 (1H, w½=8 Hz, 6α-H), 5.95 (1H, s, 4-H).

Compound (II: R¹=H; R²=α-OCOCH$_2$CH$_2$COOH; X=20,21(S)-acetonide):
M.P., 152°–155° C.
NMR (CDCl$_3$, δ): 1.27, 1.35, 1.50 (9H, 19-H,

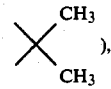

2.71 (4H, s, $$-\underset{O}{\underset{\|}{C}}CH_2CH_2\underset{O}{\underset{\|}{C}}-),$$

3.95, 4.05 (2H, AB$_q$, J$_{AB}$=9 Hz, ν$_{ΔAB}$=6.3 Hz, 21-CH$_2$—), 4.87 (1H, d, J=6 Hz, 11-H), 5.33 (1H, s, 18-H), 5.56 (1H, m, 6β-H), 5.96 (1H, d, J=2 Hz, 4-H).

Compound (II: R¹=H; R²=β-OCOCH$_2$CH$_2$COOH; X=20,21(R)-acetonide):
M.P., 118°–120° C.
NMR (CDCl$_3$, δ): 1.27, 1.40, 1.52 (9H, 19-H,

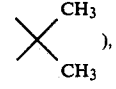

2.67 (4H, s,

—CCH₂CH₂C—),
∥  ∥
O  O 3.92, 4.21 (2H, AB_q, J_{AB}=9 Hz, ν_{ΔAB}=17.2 Hz, 21-CH₂—), 4.86 (1H, d, J=6 Hz, 11-H), 5.37 (1H, s, 18-H), 5.44 (1H, w½=8 Hz, 6α-H), 5.94 (1H, s, 4-H).

Compound (II: R¹=H; R²=α-OCOCH₂CH₂COOH; X=20,21(R)-acetonide):

NMR (CDCl₃, δ): 1.38, 1.42, 1.50 (9H, 19-H), $$\underset{CH_3}{\overset{CH_3}{\times}}),$$

2.73 (4H, s,

—CCH₂CH₂C—),
∥  ∥
O  O 3.89, 4.19 (2H, AB_q, J_{AB}=9 Hz, ν_{ΔAB}=17.2 Hz, 21-CH₂—), 4.87 (1H, d, J=6 Hz, 11-H), 5.30 (1H, s, 18-H), 5.56 (1H, m, 6β-H), 5.95 (1H, d, J=2 Hz, 4-H).

EXAMPLE 8

Preparation of immunogen and antiserum with the compound (I: R¹=H; R²=β- or α-OCOCH₂CH₂COOH):

(1) IMMUNOGEN

In the same manner as in Example 4 (1), the compound (I) (14.5 mg) obtained in Example 6 or 7 was treated to give a BSA-conjugate of the compound (I: R¹=H; R²=β-OCOCH₂CH₂COOH) (65 mg) or of the compound (I: R¹=H; R²=α-OCOCH₂CH₂COOH) (68 mg). The molar ratio of the combined hapten to the carrier protein was 11 in the former and 20 in the latter.

(2) ANTISERUM

In the same manner as in Example 4 (2), antiserum was obtained by immunizing with the immunogen obtained in (1) above. The titer of the antiserum was 9×10⁴ fold or 6×10³ fold.

EXAMPLE 9

Preparation of 11β,18-epoxy-18α,21-dihydroxy-3,20-dioxo-4-pregnen-6β-yl 4-(p-hydroxyphenethylamino)-4-oxobutyrate (I: R¹=H;

R² = β-OCOCH₂CH₂CONHCH₂CH₂—⟨benzene⟩—OH and 11β,18-epoxy-18α,21-dihydroxy-3,20-dioxo-4-pregnen-6α-yl 4-(p-hydroxyphenethylamino)-4-oxobutyrate (I:

R¹ = H; R² = α-OCOCH₂CH₂CONHCH₂CH₂—⟨benzene⟩—OH):

A solution of 11β,18;18α,20β-bisepoxy-20α,21-isopropylidenedioxy-3-oxo-4-pregnen-6β-yl 4-(p-hydroxyphenethylamino)-4-oxobutyrate (II:

R¹ = H; R² = β-OCOCH₂CH₂CONHCH₂CH₂—⟨benzene⟩—OH;

X=20,21(S)-acetonide) (13 mg) and 11β,18;18α,20α-bisepoxy-20α,21-isopropylidenedioxy-3-oxo-4-pregnen-6β-yl 4-(p-hydxoryphenethylamino)-4-oxobutyrate (II:

R¹ = H; R² = β-OCOCH₂CH₂CONHCH₂CH₂—⟨benzene⟩—OH;

X=20,21(R)-acetonide) (21 mg) in 70% acetic acid (2 ml) was stirred in argon stream at room temperature for 16 hours. The resultant mixture was combined with ice-water and extracted with ethyl acetate. The extract was washed with a saturated aqueous sodium chloride solution, dried over anhydrous sodium sulfate and concentrated under reduced pressure. The resulting residue was dissolved in methanol and treated with activated charcoal to give the compound (I: R¹=H;

R² = β-OCOCH₂CH₂CONHCH₂CH₂—⟨benzene⟩—OH)

(24 mg) as an oily substance.
Similarly, the compound (I: R¹=H;

$R^2 = \alpha\text{-OCOCH}_2\text{CH}_2\text{CONHCH}_2\text{CH}_2$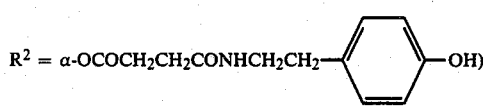—OH)

(10 mg) was obtained from 11β,18;18α,20β-bisepoxy-20α,21-isopropylidenedioxy-3-oxo-4-pregnen-6α-yl 4-(p-hydroxyphenethylamino)-4-oxobutyrate (II:

$R^1 = H; R^2 = \alpha\text{-OCOCH}_2\text{CH}_2\text{CONHCH}_2\text{CH}_2$—OH;

X=20,21(S)-acetonide) (6 mg) and 11β,18;18α,20α-bisepoxy-20β,21-isopropylidenedioxy-3-oxo-4-pregnen-6α-yl 4-(p-hydroxyphenethylamino)-4-oxobutyrate (II:

$R^1 = H; R^2 = \alpha\text{-OCOCH}_2\text{CH}_2\text{CONHCH}_2\text{CH}_2$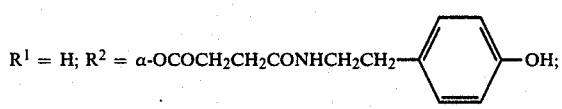—OH;

X=20,21(R)-acetonide) (8 mg).
Compound (I:

$R^1 = H; R^2 = \beta\text{-OCOCH}_2\text{CH}_2\text{CONHCH}_2\text{CH}_2$—OH):

Mass spectrum (MS m/z): 358 (M+ −237, 5%), 120 (100%).
NMR (d$_6$-acetone, δ): 1.20, 1.38, 1.42 (19-H), 4.55, 4.76 (1H, each, d, J=6 Hz, 11-H), 5.10, 5.44 (1H, each, s, 18-H), 5.39 (1H, w½=8 Hz, 6α-H), 5.83 (1H, s, 4-H), 6.76, 7.03 (4H, A$_2$B$_{2q}$, $J_{AB}$=8 Hz, $\nu_{\Delta AB}$=16.4 Hz, TLC: Rf=0.34 (acetone/chloroform=2/1).
Compound (I:

$R^1 = H; R^2 = \alpha\text{-OCOCH}_2\text{CH}_2\text{CONHCH}_2\text{CH}_2$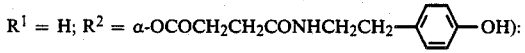—OH):

Softening point, 122° C.
Mass spectrum (MS m/z): 416 (M+ −179, 6%), 120 (100%).
NMR (D$_6$-acetone, δ): 1.20, 1.30, 1.36 (19-H), 4.57, 4.77 (1H, each, d, J=6 Hz, 11-H), 5.07, 5.42 (1H, each, s, 18-H), 5.50 (1H, m, 6β-H), 5.78 (1H, d, J=2 Hz), 6.73, 7.01 (4H, A$_2$B$_{2q}$, $J_{AB}$=8 Hz, $\nu_{\Delta AB}$=16.6 Hz,

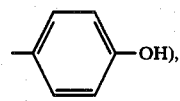—OH),

TLC: Rf=0.34 (acetone/chloroform=2/1).

REFERENCE EXAMPLE 4

Preparation of the starting material used in Example 9:

The compound (II: R$^1$=H; R$^2$=β- or

α-OCOCH$_2$CH$_2$CONHCH$_2$CH$_2$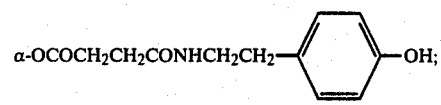—OH;

X=20,21(S)- or 20,21(R)-acetonide) used as the starting material in Example 9 was prepared by reacting the compound (II: R$^1$=H; R$^2$=β- or α-OCOCH$_2$CH$_2$COOH; X=20,21(S)- or 20,21(R)-acetonide) obtained in Reference Example 3 with tyramine in the presence of 1-hydroxybenzotriazole and dicyclohexylcarbodiimide as in Reference Example 2-1.
Compound (II:

$R^1 = H; R^2 = \beta\text{-OCOCH}_2\text{CH}_2\text{CONHCH}_2\text{CH}_2$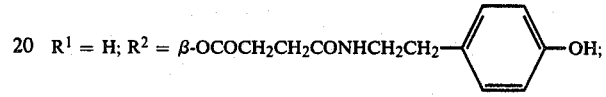—OH;

X=20,21(S)-acetonide):
M.P. (recrystallized from ether): 137°–140° C.
Mass spectrum (MS m/z): 635 (M+, <1%), 617 (M+ −18, 2%).
NMR (CDCl$_3$, δ): 1.26, 1.38, 1.47 (9H, 19-H and

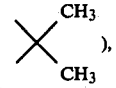

3.91, 4.02 (2H, AB$_q$, $J_{AB}$=9 Hz, $\nu_{\Delta AB}$=6.3 Hz, 21—CH$_2$—), 4.84 (1H, d, J=6 Hz, 11-H), 5.35 (1H, s, 18-H), 5.36 (1H, w½=7 Hz, 6α-H), 5.85 (1H, broad, —NH),5.93 (1H, s, 4-H), 6.78, 7.02 (4H, A$_q$B$_{2q}$, $J_{AB}$=8 Hz, $\nu_{\Delta AB}$=14.2 Hz,

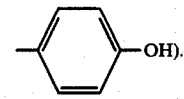—OH).

Compound (II:

$R^1 = H; R^2 = \alpha\text{-OCOCH}_2\text{CH}_2\text{CONHCH}_2\text{CH}_2$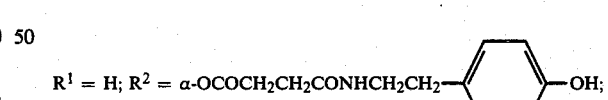—OH;

X=20,21(S)-acetonide):
Mass spectrum (MS m/z): 635 (M+, 1%).
NMR (CDCl$_3$, δ): 1.26, 1.36, 1.50 (9H, 19-H and

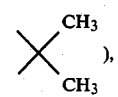

3.93, 4.03 (2H, AB$_q$, $J_{AB}$=9 Hz, $\nu_{\Delta AB}$=6.3 Hz, 21-CH$_2$—), 4.85 (1H, d, J=6 Hz, 11-H), 5.31 (1H, s, 18-H), 5.56 (1H, m, 6β-H), 5.89 (1H, d, J=2 Hz, 4-H), 6.81, 7.05 (4H, A$_q$B$_{2q}$, $J_{AB}$=8 Hz, $\nu_{\Delta AB}$=14.7 Hz,

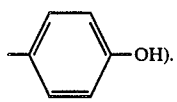

Compound (II:

X=20,21(R)-acetonide):
M.P., 125°–127° C. (recrystallized from ether).
Mass spectrum (MS m/z): 635 (M+, <1%), 617 (M+−18, 2%).
NMR (CDCl₃, δ): 1.26, 1.39, 1.50 (9H, 19-H and

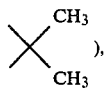

3.87, 4.16 (2H, AB$_q$, J$_{AB}$=9 Hz, ν$_{\Delta AB}$=17.2 Hz, 21-CH₂—), 4.83 (1H, d, J=6 Hz, 11-H), 5.33 (1H, s, 18-H), 5.37 (1H, w$\frac{1}{2}$=7 Hz, 6α-H), 5.86 (1H, broad, —NH), 5.93 (1H, s, 4-H), 6.78, 7.01 (4H, A$_q$B$_{29}$, J$_{AB}$=8 Hz, ν$_{\Delta AB}$=14.2 Hz,

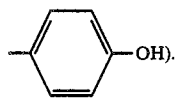

Compound (II:

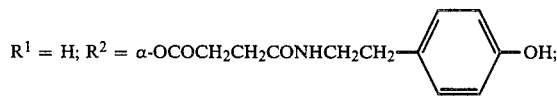

X=20,21(R)-acetonide):
M.P., 130°–133° C. (recrystallized from ether).
Mass spectrum (MS m/z): 635 (M+, <1%).
NMR (CDCl₃, δ): 1.27, 1.36, 1.50 (9H, 19-H and

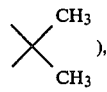

3.91, 4.20 (2H, AB$_q$, J$_{AB}$=9 Hz, ν$_{\Delta AB}$=17.2 Hz, 21-CH₂—), 4.85 (1H, d, J=6 Hz, 11-H), 5.31 (1H, s, 18-H), 5.56 (1H, m, 6β-H), 5.91 (1H, d, J=2 Hz, 4-H), 6.82, 7.06 (4H, A$_q$B$_{2q}$, J$_{AB}$=8 Hz, ν$_{\Delta AB}$=14.4 Hz,

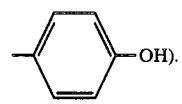

EXAMPLE 10

Labelling of the compound (I:

R¹ = H; R² = β- or

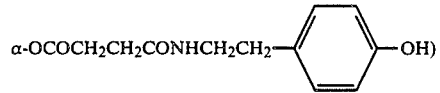

with ¹²⁵I:

The compound (I:

R¹ = H; R² = β- or

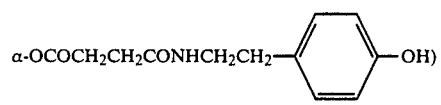

prepared in Example 9 was treated as in Example 5-1 to give ¹²⁵I-labelled compound (I: R¹=H;

R² = β-OCOCH₂CH₂CONHCH₂CH₂—⟨phenyl⟩—OH)

(330 μCi) or ¹²⁵I-labelled compound (I: R¹=H;

R² = α-OCOCH₂CH₂CONHCH₂CH₂—⟨phenyl⟩—OH)

Figure 4:
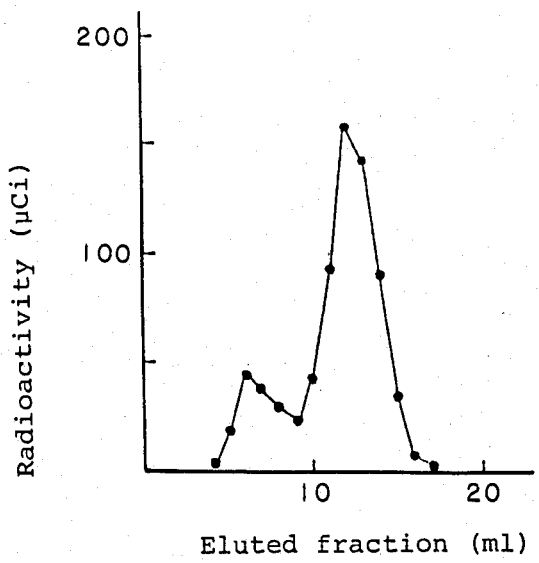
Figure 5:
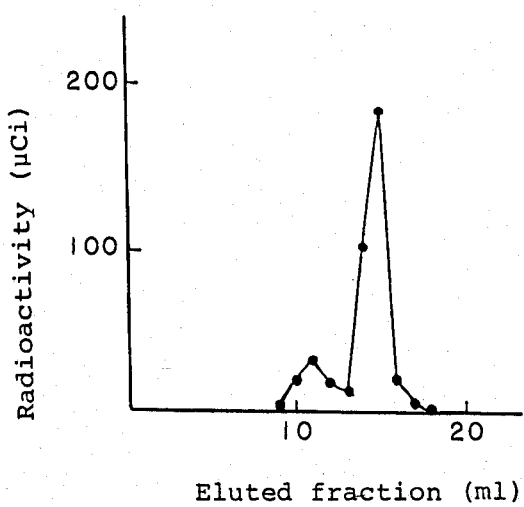

(600 μCi). The chromatograms (elution curves) are shown in FIGS. 4 and 5 of the accompanying drawings.

REFERENCE EXAMPLE 5

Apart from the ALD-labelled compounds as described in Examples 5 and 10, 11β,18-epoxy-18α,21-dihydroxy-4-pregnene-3,20-dione 3-{O-[N-(p-hydroxyphenethyl)carbamoylmethyl]oxime} (VI) was radioiodinated by the Chloramin-T method to give ¹²⁵I-labelled compound (VI), of which the specific radioactivity was 680 Ci/mmol.

EXAMPLE 11-1

RIA of serum-ALD:

(1) PROCEDURE

Serum (100 μl) was sampled in a test tube, and a buffer solution (0.1M citrate buffer, pH 5.0, containing 0.1% bovine serum γ-globulin) containing ¹²⁵I-labelled ALD (2.2×10⁴ dpm) (100 μl) prepared in Examples 5, 10 or Reference Example 5, a solution of 8-anilinonaphthalene-1-sulfonic acid (625 mg/ml) (400 μl) and one of various antiserum solutions (prepared in Examples 4 and 8) at dilution ratios as defined below were added thereto. The resulting mixture was incubated at 4° C. for 16 hours. The mixture was shaken with 25% polyethyleneglycol 6000 solution (1 ml) for 10 seconds and then centrifuged (2250×q, 20 minutes). The supernatant liquid was removed with suction and the precipitate was assayed for radioactivity with a well-type scintillation counter.

| Antiserum | Dilution fold |
| --- | --- |
| Anti-Compound<br>(I: $R^1$ = SCH$_2$COOH; $R^2$ = H)—BSA | $3 \times 10^3$ |
| Anti-Compound<br>(I: $R^1$ = H; $R^2$ = β-OCOCH$_2$CH$_2$COOH)—BSA | $2.5 \times 10^4$ |
| Anti-Compound<br>(I: $R^1$ = H; $R^2$ = α-OCOCH$_2$CH$_2$COOH)—BSA | $4 \times 10^4$ |

(2) STANDARD CURVE

Figure 6:
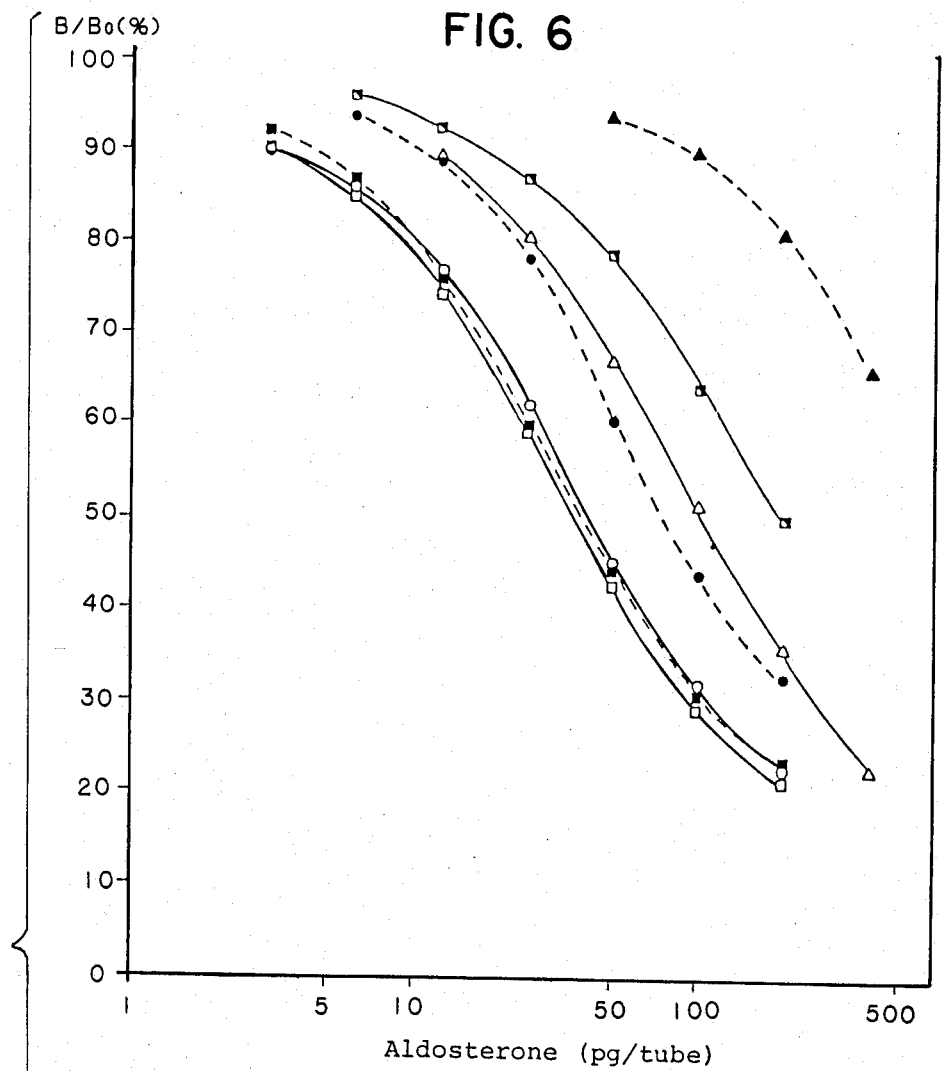

A standard curve was prepared according to the method as described in (1) above using various ALD standard solutions (0–5000 pg/ml) as shown in FIG. 6, in which Bo is the radioactivity of the antigen-antibody bound product obtained in the absence of non-radioactive ALD and B is that of the antigen-antibody bound product obtained in the presence of non-radioactive ALD.

(3) CROSS REACTIVITY

Results obtained in assays for cross reactivity between various substituted aldosterones obtained according to the present invention and other steroids (according to the method as described in (1) above) are summarized in the following table:

| Steroid | Anti-Compound (I: R¹ = H; R² = H)—BSA $^{125}$I-Compound (I: R¹ = H; R² = α-OCOCH₂CONHCH₂—⟨OH⟩) | Anti-Compound (I: R¹ = H; R² = H)—BSA $^{125}$I-Compound (VI) | Anti-Compound (I: R¹ = H; R² = α-OCOCH₂CH₂COOH)—BSA $^{125}$I-Compound (I: R¹ = H; SCH₂CONHCH₂—⟨OH; R² = H⟩) | Anti-Compound (I: R¹ = H; R² = α-OCOCH₂CH₂COOH)—BSA $^{125}$I-Compound (VI) | Anti-Compound (I: R¹ = H; R² = β-COCH₂CH₂COOH)—BSA $^{125}$I-Compound (I: R¹ = H; SCH₂CONHCH₂—⟨OH; R² = H⟩) |
|---|---|---|---|---|---|
| Aldosterone | 100 | 100 | 100 | 100 | 100 |
| Corticosterone | 0.03 | — | 0.00009 | 0.0001 | 0.003 |
| 11-Deoxycorticosterone | 0.15 | — | 0.0002 | 0.0003 | 0.007 |
| Cortisone | 0.0004 | — | 0.00004 | — | 0.003 |
| Cortisol | 0.00007 | 0.00009 | <0.00003 | <0.00008 | 0.0001 |
| Progesterone | 0.004 | — | <0.0003 | 0.00009 | 0.0003 |
| 11α-Hydroxyprogesterone | 0.0004 | — | <0.00003 | — | — |
| 17α-Hydroxyprogesterone | 0.00008 | — | <0.00004 | — | — |
| 20α-Hydroxyprogesterone | 0.0003 | — | <0.00006 | — | — |
| Testosterone | 0.002 | — | <0.0002 | — | <0.0001 |
| 17β-Estradiol | <0.00004 | — | <0.0002 | — | <0.0001 |

EXAMPLE 11-2

Figure 7:
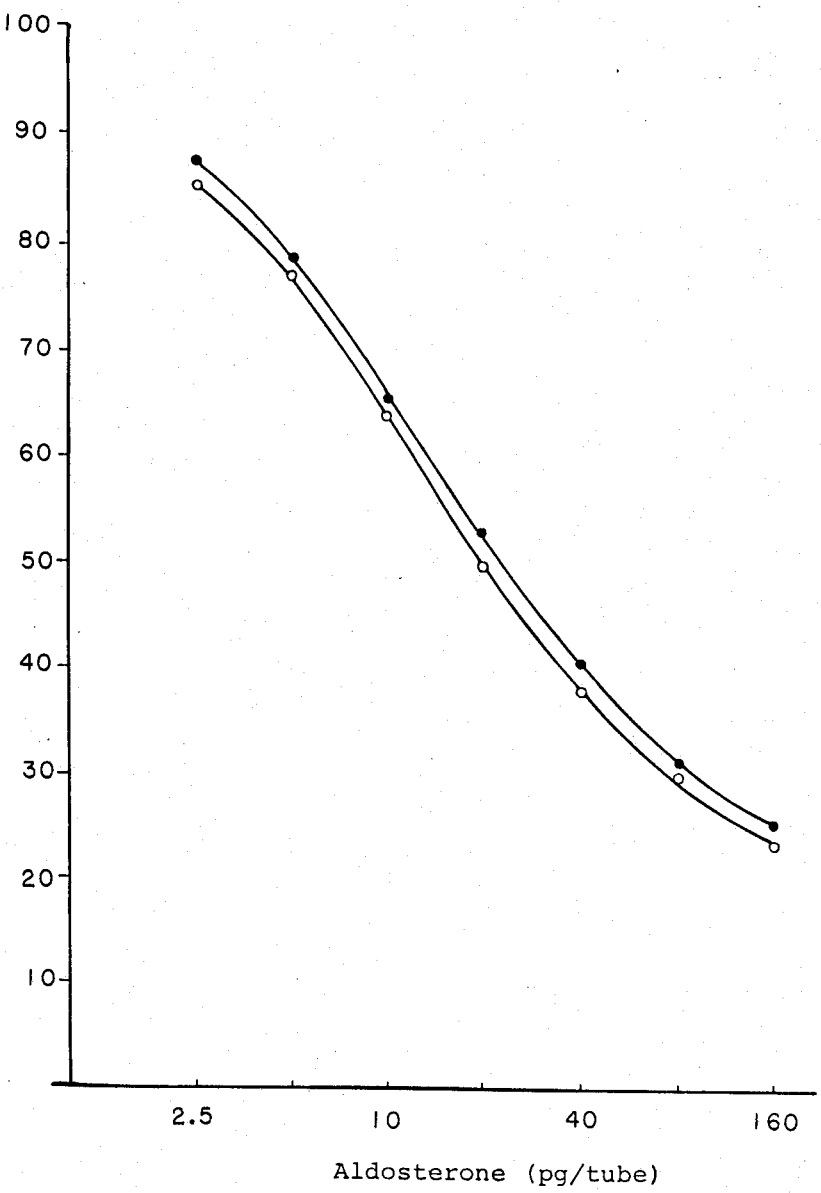
Figure 7:
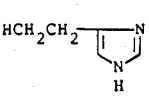
Figure 7:

RIA of serum-ALD:

According to the procedure as described in Example 11-1, a B/Bo standard curve as shown in FIG. 7 of the accompanying drawing was prepared using the labelled compound obtained in Example 5-2 and anti-Compound (I: $R^1$=H; $R^2$=α-OCOCH$_2$CH$_2$COOH)-BSA.

EXAMPLE 12

EIA of serum-ALD:

(1) PREPARATION OF ENZYME-LABELLED ANTIGEN

Each of the carboxylic acid derivatives of ALD, i.e. Compound (I: $R^1$=SCH$_2$COOH; $R^2$=H) in Example 1, Compound (I: $R^1$=H; $R^2$=β-SCH$_2$COOH) in Example 2, Compound (I: $R^1$=H; $R^2$=β-OCOCH$_2$CH$_2$COOH) in Example 6, Compound (I: $R^1$=H; $R^2$=α-OCOCH$_2$CH$_2$COOH) in Example 7 and 11β,18-epoxy-18α,21-dihydroxy-4-pregnene-3,20-dione 3-(O-carboxymethyl)oxime (VI) which is known, was dissolved in dioxane (400 μl). To this solution were added tri-n-butylamine (6.3 μmol) in dioxane (50 μl) and, with cooling at 10°–12° C., isobutyl chloroformate (6 μmol) in dioxane (50 μl). The mixture was stirred for 30 minutes to afford an active ester solution.

Separately, β-D-galactosidase (30 U/mg, Boehringer Mannheim GmbH) (2 mg) was dissolved in 10% dioxane (3.5 ml), and the resultant solution was adjusted to pH 9.2 with 0.1N aqueous sodium hydroxide. To this solution was added dropwise the activated ester solution obtained above with ice-cooling and stirring. After 5 minutes, the mixture was adjusted to pH 8.5. Stirring was continued at 4° C. for 4 hours. Then, the mixture was dialyzed against 0.01M phosphate buffer (pH 7.4) containing 0.05% sodium azide for 2 days. The obtained β-D-galactosidase/ALD-derivative conjugate (hereinafter referred to as VIIa, VIIb, VIIc, VIId or VIIe, according to the order of the compound to be labelled) was used as the enzyme-labelled antigen.

(2) EIA

The standard ALD solution (100 μl) was sampled in a test tube. To this solution were added 0.1M phosphate buffer (pH 7.4) (300 μl), a diluted enzyme-labelled antigen solution (obtained by diluting the enzyme-labelled antigen in 100,000 folds) (100 μl) and, after mixing, a solution of antiserum (500 μl), and the resultant mixture was allowed to stand at 4° C. for 5 hours.

Then, Immunobead (trade name, Bio-Rad Co., Ltd., 1 mg/ml) (100 μl) was added to the mixture, which was, after allowed to stand at 4° C. for 1 hour, centrifuged (2000×g, 5 minutes). The supernatant liquid was removed with suction. The precipitate was washed twice with 0.1M phosphate buffer (pH 7.4) and resuspended in 0.01M phosphate buffer (pH 7.3) containing 0.14M sodium chloride, 0.001M magnesium chloride, 0.05% sodium azide and 0.5% BSA. To this suspension was added 4-methylumbellipheryl-β-D-galactoside solution (80 μg/ml) (400 μl) and the obtained mixture was incubated at 37° C. for 30 minutes. The reaction was stopped by adding 0.1M glycine buffer (pH 10.5) (3 ml) thereto, and the mixture was assayed for intensity of fluorescence (excitation at 360 nm and fluorescence at 448 nm).

The assay for ALD in serum was conducted in the same manner as above but using a specimen of serum (100 μl) and 8-anilinonaphthalene-1-sulfonic acid solution (800 μ/ml) (300 μl) in place of the standard solution (100 μl) and the buffer (300 μl). Possible combinations of enzyme-labelled antigen and antiserum are shown in the following table by marking with a circle:

| Antiserum | Enzyme-labelled antigen | | | | |
|---|---|---|---|---|---|
| | VIIa | VIIb | VIIc | VIId | VIIe |
| Anti-Compound (I: $R^1$ = SCH$_2$COOH: $R^2$ = H)—BSA (Example 4) | O | O | O | | O |
| Anti-Compound (I: $R^1$ = H; $R^2$ = β-OCOCH$_2$CH$_2$COOH)—BSA (Example 8) | O | O | | | O |
| Anti-Compound (I: $R^1$ = H; $R^2$ = α-OCOCH$_2$CH$_2$COOH)—BSA (Example 8) | O | O | | | O |

What is claimed is:

1. A substituted aldosterone of the formula:

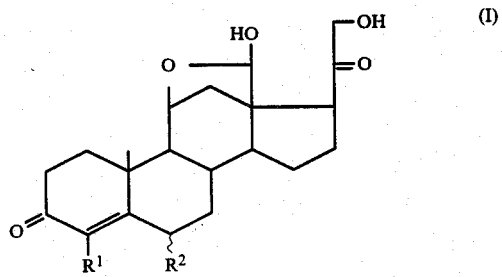

wherein either one of $R^1$ and $R^2$ is hydrogen and the other is —S(CH$_2$)$_m$COR$^3$ or —OCO(CH$_2$)$_n$COR$^3$, provided that when $R^1$ is hydrogen, $R^2$ is —S(CH$_2$)$_m$COR$^3$ or —OCO(CH$_2$)$_n$COR$^3$ and when $R^2$ is hydrogen, $R^1$ is —S(CH$_2$)$_m$COR$^3$; m being an integer from 1 to 3, n being an integer from 1 to 5 and $R^3$ being a residue of tyramine, a residue of iodinated tyramine, a residue of tyrosine lower alkyl ester, a residue of iodinated tyrosine lower alkyl ester, a residue of histamine, a residue of iodinated histamine, a residue of histidine, a residue of iodinated histidine, a residue of 7-aminoheptanoyltyrosine lower alkyl ester, a residue of iodinated 7-aminoheptanoyltyrosine lower alkyl ester, or its (18-20)-acetal 20,21-ketonide.

2. The substituted aldosterone according to claim 1, wherein $R^3$ is a residue of radioiodinated tyramine, radioiodinated histamine, or radioiodinated tyrosine lower alkyl ester or its (18-20)-acetal 20,21-ketonide.

* * * * *